(12) United States Patent
Simpson et al.

(10) Patent No.: US 12,011,265 B2
(45) Date of Patent: Jun. 18, 2024

(54) METHOD OF MAKING A SENSOR DEVICE

(71) Applicant: DexCom, Inc., San Diego, CA (US)

(72) Inventors: Peter C. Simpson, Cardiff, CA (US); Jennifer Blackwell, San Diego, CA (US); Sebastian Böhm, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 1491 days.

(21) Appl. No.: 16/359,765

(22) Filed: Mar. 20, 2019

(65) Prior Publication Data

US 2019/0209057 A1 Jul. 11, 2019

Related U.S. Application Data

(63) Continuation of application No. 13/780,808, filed on Feb. 28, 2013, now abandoned.
(Continued)

(51) Int. Cl.
*H01S 4/00* (2006.01)
*A61B 5/00* (2006.01)
(Continued)

(52) U.S. Cl.
CPC ........ *A61B 5/1473* (2013.01); *A61B 5/14503* (2013.01); *A61B 5/14532* (2013.01); *A61B 5/14865* (2013.01); *A61B 5/4839* (2013.01); *A61B 5/6848* (2013.01); *A61B 17/3468* (2013.01); *A61B 2017/00004* (2013.01); *A61B 2562/12* (2013.01); *A61L 31/08* (2013.01); *B21G 1/003* (2013.01); *B21G 1/006* (2013.01); *B21G 1/12* (2013.01); *Y10T 29/49002* (2015.01)

(58) Field of Classification Search
CPC ............ A61B 17/3468; A61B 2017/00; A61B 2562/12; A61B 5/14503; A61B 5/14532; A61B 5/1473; A61B 5/14865; A61L 31/08; Y10T 29/49002; B21G 1/003; B21G 1/006; B21G 1/12
See application file for complete search history.

(56) References Cited

U.S. PATENT DOCUMENTS 5,190,529 A  3/1993  McCrory et al.
5,299,571 A  4/1994  Mastrototaro
(Continued)

FOREIGN PATENT DOCUMENTS

EP  0789540 B1  9/2001
EP  0729366 B1  7/2002
(Continued)

OTHER PUBLICATIONS

Gunatillake et al., "Recent developments in biodegradable synthetic polymers", Biotechnology Annual Review (2006) 12:301-347.
(Continued)

*Primary Examiner* — Paul D Kim
(74) *Attorney, Agent, or Firm* — Snell & Wilmer LLP

(57) ABSTRACT

Sensor devices including dissolvable tissue-piercing tips are provided. The sensor devices can be used in conjunction with dissolvable needles configured for inserting the sensor devices into a host. Hardening agents for strengthening membranes on sensor devices are also provided. Methods of using and fabricating sensor devices are also provided.

20 Claims, 11 Drawing Sheets

Related U.S. Application Data

(60) Provisional application No. 61/713,338, filed on Oct. 12, 2012.

(51) Int. Cl.
*A61B 5/145* (2006.01)
*A61B 5/1473* (2006.01)
*A61B 5/1486* (2006.01)
*A61B 17/34* (2006.01)
A61B 17/00 (2006.01)
A61L 31/08 (2006.01)
B21G 1/00 (2006.01)
B21G 1/12 (2006.01)

(56) References Cited

U.S. PATENT DOCUMENTS

| | | |
|---|---|---|
| 5,390,671 A | 2/1995 | Lord et al. |
| 5,391,250 A | 2/1995 | Chenay et al. |
| 5,527,288 A | 6/1996 | Gross et al. |
| 5,569,186 A | 10/1996 | Lord et al. |
| 5,746,217 A | 5/1998 | Erickson et al. |
| 5,800,420 A | 9/1998 | Gross et al. |
| 5,807,306 A | 9/1998 | Shapland et al. |
| 5,807,375 A | 9/1998 | Gross et al. |
| 5,820,622 A | 10/1998 | Gross et al. |
| 5,848,991 A | 12/1998 | Gross et al. |
| 5,885,251 A | 3/1999 | Luther |
| 5,931,814 A | 8/1999 | Alex et al. |
| 5,954,643 A | 9/1999 | Van Antwerp et al. |
| 5,964,744 A | 10/1999 | Balbierz et al. |
| 5,997,501 A | 12/1999 | Gross et al. |
| 6,071,294 A | 6/2000 | Simons et al. |
| 6,103,033 A | 8/2000 | Say et al. |
| 6,132,449 A | 10/2000 | Lum et al. |
| 6,175,752 B1 | 1/2001 | Say et al. |
| 6,186,982 B1 | 2/2001 | Gross et al. |
| 6,275,717 B1 | 8/2001 | Gross et al. |
| 6,360,888 B1 | 3/2002 | McIvor et al. |
| 6,405,066 B1 | 6/2002 | Essenpreis et al. |
| 6,424,847 B1 | 7/2002 | Mastrototaro et al. |
| 6,520,326 B2 | 2/2003 | McIvor et al. |
| 6,537,242 B1 | 3/2003 | Palmer |
| 6,558,320 B1 | 5/2003 | Causey et al. |
| 6,692,456 B1 | 2/2004 | Eppstein et al. |
| 6,712,776 B2 | 3/2004 | Latterell et al. |
| 6,892,085 B2 | 5/2005 | McIvor et al. |
| 6,997,886 B2 | 2/2006 | Latterell et al. |
| 7,029,444 B2 | 4/2006 | Shin et al. |
| 7,041,057 B1 | 5/2006 | Faupel et al. |
| 7,146,202 B2 | 12/2006 | Ward et al. |
| 7,310,543 B2 | 12/2007 | Smart et al. |
| 7,381,184 B2 | 6/2008 | Funderburk et al. |
| 7,842,210 B2 * | 11/2010 | Chen ............... B29C 70/74 |
| | | 264/279.1 |
| 8,114,006 B2 | 2/2012 | Cox et al. |
| 8,187,433 B2 | 5/2012 | Ward et al. |
| 8,224,410 B2 | 7/2012 | Hadviary et al. |
| 8,512,243 B2 | 8/2013 | Stafford |
| 8,694,069 B1 | 4/2014 | Kosa et al. |
| 9,357,951 B2 * | 6/2016 | Simpson ............ A61B 5/14532 |
| 9,480,421 B2 | 11/2016 | Stafford |
| 9,844,328 B2 | 12/2017 | Simpson et al. |
| 10,448,872 B2 * | 10/2019 | Wolfe ............... A61B 5/14542 |
| 10,932,709 B2 | 3/2021 | Simpson et al. |
| 2001/0016702 A1 | 8/2001 | Benjamin |
| 2002/0022855 A1 | 2/2002 | Bobroff |
| 2002/0072720 A1 | 6/2002 | Hague et al. |
| 2002/0137998 A1 | 9/2002 | Smart et al. |
| 2004/0138541 A1 | 7/2004 | Ward et al. |
| 2004/0138543 A1 | 7/2004 | Russell et al. |
| 2004/0254433 A1 | 12/2004 | Bandis et al. |
| 2005/0004438 A1 | 1/2005 | Ward et al. |
| 2005/0143635 A1 | 6/2005 | Kamath et al. |
| 2006/0004272 A1 | 1/2006 | Shah et al. |
| 2006/0008500 A1 * | 1/2006 | Chavan ............... B82Y 15/00 |
| | | 607/2 |
| 2006/0020192 A1 | 1/2006 | Brister et al. |
| 2006/0021092 A1 | 1/2006 | McCourt et al. |
| 2006/0030824 A1 | 2/2006 | Hunn et al. |
| 2006/0030833 A1 | 2/2006 | Harris |
| 2006/0211921 A1 | 9/2006 | Brauker et al. |
| 2006/0289307 A1 | 12/2006 | Yu et al. |
| 2007/0027370 A1 | 2/2007 | Brauker et al. |
| 2007/0038014 A1 | 2/2007 | Cox et al. |
| 2007/0078322 A1 | 4/2007 | Stafford |
| 2007/0129619 A1 | 6/2007 | Ward et al. |
| 2007/0191737 A1 | 8/2007 | Freeman et al. |
| 2007/0235331 A1 | 10/2007 | Simpson et al. |
| 2007/0290619 A1 | 12/2007 | Kang |
| 2008/0033269 A1 | 2/2008 | Zhang |
| 2008/0076974 A1 | 3/2008 | Yamazaki et al. |
| 2008/0249383 A1 | 10/2008 | Sass et al. |
| 2008/0249385 A1 | 10/2008 | Phan |
| 2009/0105605 A1 | 4/2009 | Abreu |
| 2009/0131768 A1 | 5/2009 | Simpson et al. |
| 2009/0171302 A1 | 7/2009 | Eramo |
| 2010/0121307 A1 | 5/2010 | Lockard et al. |
| 2010/0160756 A1 | 6/2010 | Petisce et al. |
| 2010/0219085 A1 | 9/2010 | Oviatt, Jr. |
| 2010/0286496 A1 | 11/2010 | Simpson et al. |
| 2011/0073475 A1 | 3/2011 | Kastanos et al. |
| 2011/0077490 A1 | 3/2011 | Simpson et al. |
| 2011/0230735 A1 | 9/2011 | Wolfe |
| 2012/0028283 A1 | 2/2012 | Hoss et al. |
| 2012/0190952 A1 | 7/2012 | Stafford |
| 2012/0253145 A1 | 10/2012 | Stafford et al. |
| 2013/0056144 A1 | 3/2013 | Kotzan et al. |
| 2013/0253289 A1 | 9/2013 | Hadváry et al. |
| 2013/0253293 A1 | 9/2013 | Ocvirk et al. |
| 2013/0253438 A1 | 9/2013 | Badawi et al. |
| 2014/0107450 A1 * | 4/2014 | Simpson ............ A61B 5/1473 |
| | | 600/365 |
| 2014/0213866 A1 | 7/2014 | Simpson et al. |
| 2015/0216462 A1 | 8/2015 | Kastanos et al. |
| 2016/0089065 A1 | 3/2016 | Simpson et al. |
| 2016/0113556 A1 | 4/2016 | Simpson et al. |

FOREIGN PATENT DOCUMENTS

| | | |
|---|---|---|
| JP | 2006286986 A * | 10/2006 |
| WO | WO 1998/56293 | 12/1998 |
| WO | WO 2002/047745 | 6/2002 |
| WO | WO 2011/110202 | 9/2011 |

OTHER PUBLICATIONS

Miller et al., "Multiplexed microneedle-based biosensor array for characterization of metabolic acidosis", Talanta (2012) 88:739-742.

Valdés-Ramírez et al., "Multiplexed and switchable release of distinct fluids from microneedle platforms via conducting polymer nanoactuators for potential drug delivery", Sensors and Actuators B (2012) 161:1018-1024.

Windmiller et al., "Bicomponent Microneedle Array Biosensor for Minimally-Invasive Glutamate Monitoring", Electroanalysis (2011) 23(10):2302-2309.

Windmiller et al., "Microneedle array-based carbon paste amperometric sensors and biosensors", Analyst (2011) 136:1846-1851.

Buckingham M.D.B., et al., "Preventing Hypoglycemia Using Predictive Alarm Algorithms and Insulin Pump Suspension," Diabetes Technology & Therapeutics, vol. 11, No. 2, 2009, pp. 93-97.

Extended European Search Report for Application No. 20157783.0 dated Jul. 14, 2020, 11 pages.

* cited by examiner

METHOD OF MAKING A SENSOR DEVICE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/780,808, filed Feb. 28, 2013, now abandoned, which claims the benefit of U.S. Provisional Application No. 61/713,338 filed Oct. 12, 2012. Each of the aforementioned applications is incorporated by reference herein in its entirety, and each is hereby expressly made a part of this specification.

TECHNICAL FIELD

The present embodiments relate to systems and methods for measuring an analyte concentration in a host.

BACKGROUND

Diabetes mellitus is a disorder in which the pancreas cannot create sufficient insulin (Type 1 or insulin dependent) and/or in which insulin is not effective (Type 2 or non-insulin dependent). In the diabetic state, the victim suffers from high blood sugar, which may cause an array of physiological derangements associated with the deterioration of small blood vessels, for example, kidney failure, skin ulcers, or bleeding into the vitreous of the eye. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements may be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a raw signal that is transmitted to electronics associated with the sensor. The raw signal is converted into an output value that is displayed on a display. The output value that results from the conversion of the raw signal is typically expressed in a form that provides the user with meaningful information, such as blood glucose expressed in mg/dL.

SUMMARY

The various present embodiments have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One aspect of the present embodiments includes the realization that tack sensors include a sharpened tip that remains implanted in the tissue throughout the usable life of the sensor. Leaving the sharpened tip in vivo for an extended period of time may cause trauma to surrounding tissue, leading to scarring and inhibition of wound healing. Some of the present embodiments provide solutions to this problem.

In recognition of the foregoing problem, in a first aspect certain of the present embodiments comprise a sensor device for measuring an analyte concentration in a host, the sensor device comprising: a sensor unit comprising a sensor body, at least one electrode, and a membrane covering at least a portion of the at least one electrode, the sensor body having a blunt tip; a piercing element comprising a material that rapidly dissolves upon insertion into the host, the piercing element abutting the sensor tip and being capable of piercing tissue; and a mounting unit spaced from the sensor tip and configured to support the sensor device on an exterior surface of the host's skin.

In an embodiment of the first aspect, the piercing element is secured to the sensor tip.

In an embodiment of the first aspect, the piercing element is adhered to the sensor tip.

In an embodiment of the first aspect, the piercing element is not secured to the sensor tip, but is maintained in abutting contact therewith.

In an embodiment of the first aspect, a sleeve surrounding the sensor tip and the piercing element maintains the abutting contact.

In an embodiment of the first aspect, the piercing element comprises a coating that covers at least a portion of the sensor body including the sensor tip.

In an embodiment of the first aspect, the coating comprises a sharp coating tip.

In an embodiment of the first aspect, the material of the piercing element comprises a material that suppresses wounding.

In an embodiment of the first aspect, the material of the piercing element comprises a material that promotes rapid wound healing.

In an embodiment of the first aspect, the material of the piercing element comprises a material that induces osmotic pressure or oncotic pressure.

In an embodiment of the first aspect, the material of the piercing element comprises one or more drugs.

In an embodiment of the first aspect, the material of the piercing element comprises a vascular endothelial growth factor (VEGF).

In an embodiment of the first aspect, the material of the piercing element comprises at least one of a salt, a metallic salt, a sugar, a synthetic polymer, polylactic acid, polyglycolic acid, or a polyphosphazene.

In an embodiment of the first aspect, the material of the piercing element biodegrades/dissolves within a first day after insertion into the host.

In an embodiment of the first aspect, the material of the piercing element biodegrades/dissolves within three hours after insertion into the host.

In an embodiment of the first aspect, the piercing element does not extend past the sensor tip in the direction of the mounting unit, or extends only a nominal amount in said direction.

In an embodiment of the first aspect, the piercing element extends past the sensor tip in the direction of the mounting unit, but stops short of the electrode.

In an embodiment of the first aspect, the mounting unit comprises a guiding portion configured to guide insertion of the sensor unit through the host's skin and to support a column strength of the sensor body such that the sensor unit is capable of being inserted through the host's skin without substantial buckling.

In an embodiment of the first aspect, the at least one electrode comprises a working electrode and a reference electrode.

In an embodiment of the first aspect, the sensor body further comprises a support member configured to protect the membrane from damage during insertion of the sensor unit.

In an embodiment of the first aspect, the at least one electrode is the support member.

In an embodiment of the first aspect, the support member is configured to support at least a portion of the at least one electrode.

In an embodiment of the first aspect, the support member is configured to substantially surround the at least one electrode.

In an embodiment of the first aspect, the mounting unit comprises a sensor electronics unit operatively and detachably connected to the sensor body.

In an embodiment of the first aspect, the sensor electronics unit is configured to be located over a sensor insertion site.

Also in recognition of the foregoing problem, in a second aspect certain of the present embodiments comprise a method of making a sensor device, the method comprising: dipping a tip of a sensor into a liquid to form a coating of the liquid on the sensor tip; and withdrawing the sensor tip from the liquid while controlling parameters of the withdrawal so that the coating forms a sharp point extending from the sensor tip, the sharp point being capable of piercing tissue.

In an embodiment of the second aspect, the parameters include at least one of a length (L) of the sensor that is wetted by the liquid, a viscosity of the liquid, and a withdrawal rate.

In an embodiment of the second aspect, L is in the range of 0.1-4 mm.

In an embodiment of the second aspect, L is 2-3 mm.

In an embodiment of the second aspect, the viscosity is below 100 cP.

In an embodiment of the second aspect, the withdrawal rate is 20-30 in/sec.

In an embodiment of the second aspect, the method further comprises curing the coating.

In an embodiment of the second aspect, the curing comprises UV (or heat) cross-linking, irradiating, drying, or heating.

In an embodiment of the second aspect, the method further comprises using a tip mold or draw-through fixture that clamps and cures in one step in order to form a sharp cone shape.

In an embodiment of the second aspect, the method further comprises applying a voltage to the coating while it is being cured.

In an embodiment of the second aspect, the method further comprises heating the coating and drawing it out like glass.

Another aspect of the present embodiments includes the realization that in some current methods for sensor insertion the sensor is received within the lumen of an insertion needle. The needle, which has greater column strength than the sensor, bears the frictional forces that occur during insertion. Once the sensor is in place in the tissue, the needle is removed. The need to remove the needle adds complexity to the insertion process, including the need to electrically connect the sensor to sensor electronics after insertion. Some of the present embodiments provide solutions to this problem.

In recognition of the foregoing problem, in a third aspect certain of the present embodiments comprise a sensor device for measuring an analyte concentration in a host, the sensor device comprising: a sensor unit comprising a sensor body, at least one electrode, and a membrane covering at least a portion of the at least one electrode; and a piercing element comprising a material that rapidly dissolves upon insertion into the host, the piercing element including a sharp tip capable of piercing tissue, and a lumen that receives the sensor unit.

In an embodiment of the third aspect, the sensor body has a blunt tip.

In an embodiment of the third aspect, the sensor unit is not secured to the piercing element.

In an embodiment of the third aspect, the sensor unit is secured to the piercing element.

In an embodiment of the third aspect, the material of the piercing element comprises a material that suppresses wounding.

In an embodiment of the third aspect, the material of the piercing element comprises a material that promotes rapid wound healing.

In an embodiment of the third aspect, the material of the piercing element comprises a material that induces osmotic pressure or oncotic pressure.

In an embodiment of the third aspect, the material of the piercing element comprises one or more drugs.

In an embodiment of the third aspect, the material of the piercing element comprises a vascular endothelial growth factor (VEGF).

In an embodiment of the third aspect, the material of the piercing element comprises at least one of a salt, a metallic salt, a sugar, a synthetic polymer, polylactic acid, polyglycolic acid, or a polyphosphazene.

In an embodiment of the third aspect, the material of the piercing element biodegrades/dissolves within a first day after insertion into the host.

In an embodiment of the third aspect, the material of the piercing element biodegrades/dissolves within three hours after insertion into the host.

Another aspect of the present embodiments includes the realization that the material of analyte sensor membranes is soft, and tends to peel back as the sensor advances into tissue. This problem is especially acute for sensors that are formed by a process in which they are first coated with a membrane and then sharpened at the tip. This process exposes the sensor body, and leaves a thin coating of the membrane surrounding the sides of the sensor body at the tip. Some of the present embodiments provide solutions to this problem.

In recognition of the foregoing problem, in a fourth aspect certain of the present embodiments comprise a sensor device for measuring an analyte concentration in a host, the sensor device comprising: a sensor unit comprising a sensor body, at least one electrode, and a membrane covering at least a portion of the at least one electrode; and a mounting unit spaced from the sensor tip and configured to support the sensor device on an exterior surface of the host's skin; wherein the membrane comprises a hardening agent, the hardening agent providing increased column strength to the sensor unit so that the sensor unit is capable of being inserted through the host's skin without substantial buckling.

In an embodiment of the fourth aspect, the hardening agent is integrated with the membrane.

In an embodiment of the fourth aspect, the membrane covers a tip of the sensor body.

In an embodiment of the fourth aspect, a tip of the sensor body is exposed through the membrane.

In an embodiment of the fourth aspect, the exposed tip of the sensor body comprises a material that does not react with hydrogen peroxide.

In an embodiment of the fourth aspect, the hardening agent comprises cyanoacrylate.

Also in recognition of the foregoing problem, in a fifth aspect certain of the present embodiments comprise a sensor device for measuring an analyte concentration in a host, the sensor device comprising: a sensor unit comprising a sensor body, at least one electrode, and a membrane covering at least a portion of the at least one electrode; and a mounting unit spaced from the sensor tip and configured to support the sensor device on an exterior surface of the host's skin; wherein the membrane comprises a hardening agent, the hardening agent increasing a column strength of the sensor unit and increasing an adhesion of the membrane to the at least one electrode; and wherein the membrane comprising the hardening agent allows analyte permeability.

In an embodiment of the fifth aspect, the hardening agent is suspended in a matrix.

In an embodiment of the fifth aspect, the membrane covers a tip of the sensor.

In an embodiment of the fifth aspect, a tip of the sensor is exposed through the membrane.

In an embodiment of the fifth aspect, the exposed tip of the sensor comprises a material that does not react with hydrogen peroxide.

In an embodiment of the fifth aspect, the hardening agent comprises cyanoacrylate.

Also in recognition of the foregoing problem, in a sixth aspect certain of the present embodiments comprise a method of making a sensor device, the method comprising: coating a wire with a membrane; cutting the coated wire to a desired length to thereby form a sensor tip; and exposing the coated wire to a hardening agent such that the membrane absorbs the hardening agent.

In an embodiment of the sixth aspect, exposing the coated wire comprises dipping at least the sensor tip in the hardening agent.

In an embodiment of the sixth aspect, certain of the present embodiments further comprise curing the membrane to harden the hardening agent.

In an embodiment of the sixth aspect, certain of the present embodiments further comprise sharpening the sensor tip to form a sharp point capable of piercing tissue.

In an embodiment of the sixth aspect, the sensor tip comprises a material that does not react with hydrogen peroxide.

In an embodiment of the sixth aspect, certain of the present embodiments further comprise applying a deadening agent to the sharpened sensor tip to deaden any active surfaces exposed during the sharpening step.

In an embodiment of the sixth aspect, the deadening agent comprises cyanoacrylate or silane.

In an embodiment of the sixth aspect, the deadening agent is applied using vapor deposition.

In an embodiment of the sixth aspect, the hardening agent comprises cyanoacrylate.

Also in recognition of the foregoing problem, in a seventh aspect certain of the present embodiments comprise a method of making a sensor device, the method comprising: cutting a wire to a desired length to thereby form a sensor tip; sharpening the sensor tip to form a sharp point capable of piercing tissue; coating the wire, including the sharpened sensor tip, with a membrane; and exposing the coated wire to a hardening agent such that the membrane absorbs the hardening agent.

In an embodiment of the seventh aspect, exposing the coated wire comprises dipping at least the sensor tip in the hardening agent.

In an embodiment of the seventh aspect, certain of the present embodiments further comprise curing the membrane to harden the hardening agent.

In an embodiment of the seventh aspect, the hardening agent comprises cyanoacrylate.

BRIEF DESCRIPTION OF THE DRAWINGS

The various present embodiments now will be discussed in detail with an emphasis on highlighting the advantageous features. These embodiments depict the novel and non-obvious sensors for continuous analyte monitoring, and related methods shown in the accompanying drawings, which are for illustrative purposes only. These drawings include the following figures, in which like numerals indicate like parts.

DETAILED DESCRIPTION

Figure 1:
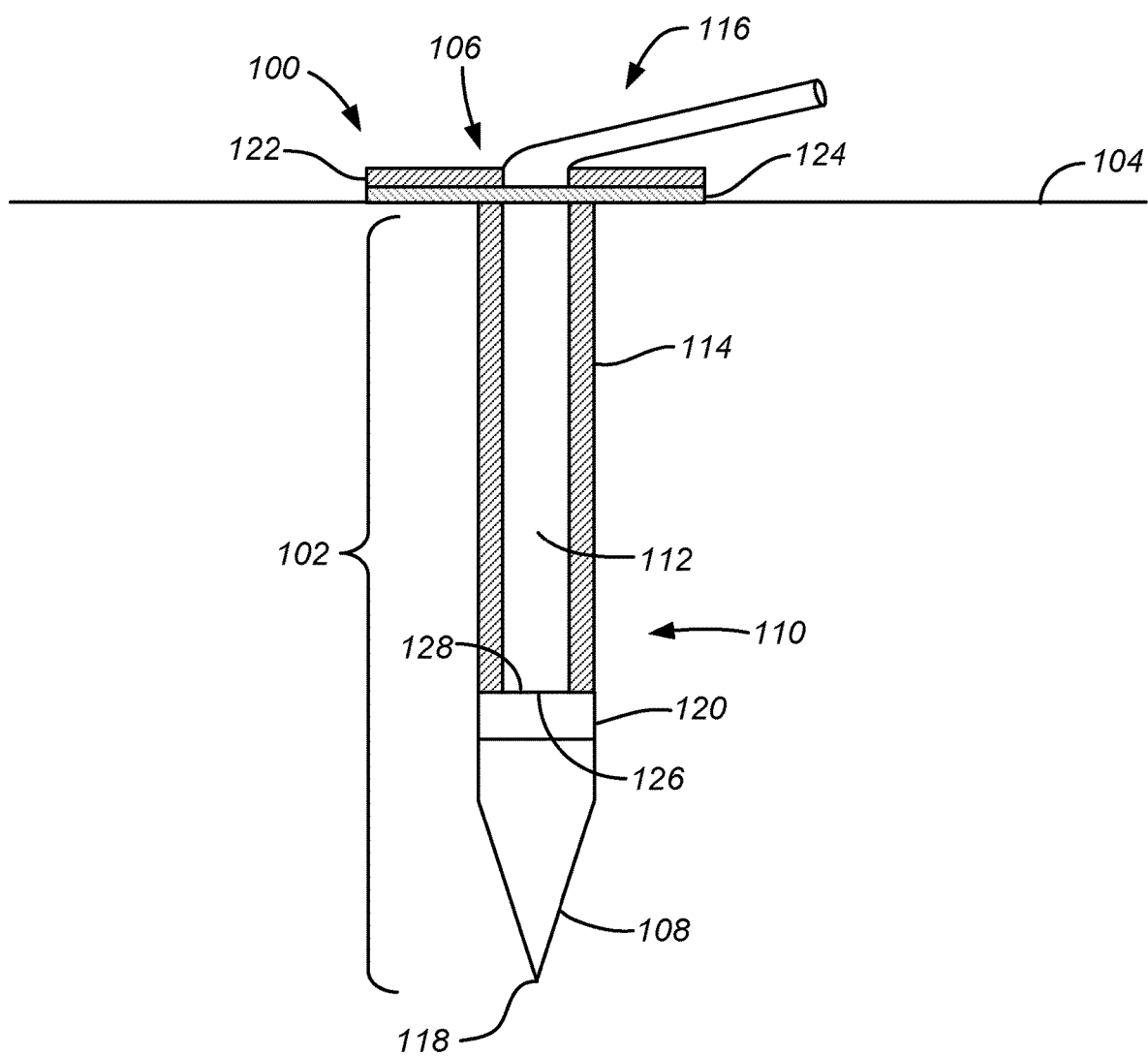
FIG. 1 is a schematic cross-sectional view of a continuous analyte sensor according to the present embodiments.

The following detailed description describes the present embodiments with reference to the drawings. In the drawings, reference numbers label elements of the present embodiments. These reference numbers are reproduced below in connection with the discussion of the corresponding drawing features.

The drawings and their descriptions may indicate sizes, shapes and configurations of the various components. Such depictions and descriptions should not be interpreted as limiting. Alternative sizes, shapes and configurations are also contemplated as within the scope of the present embodiments. Also, the drawings, and their written descriptions, indicate that certain components of the apparatus are formed integrally, and certain other components are formed as separate pieces. Components shown and described herein as being formed integrally may in alternative embodiments be formed as separate pieces. Further, components shown and described herein as being formed as separate pieces may in alternative embodiments be formed integrally. As used herein the term integral describes a single unitary piece.

Overview

The embodiments described herein provide various mechanisms for directly inserting a transcutaneous sensor into a host without the use of a separate applicator, i.e., other than the sensor device itself. Direct press insertion of a transcutaneous sensor (e.g., an electrode) having a wire-like geometry, especially a fine wire, may be technically challenging because of buckling risks associated with the sensor. Direct press insertion of a sensor also presents challenges relating to damage during the insertion process to the membrane disposed on the sensor. Without membrane protection, the membrane may be stripped off from the sensor or be mechanically damaged during the insertion process. The embodiments described herein are designed to overcome the aforementioned challenges by providing miniaturized sensor devices capable of providing structural support (e.g., in the form of mechanical/structural properties such as column strength) for direct insertion of a transcutaneous sensor and capable of protecting the membrane from damage during the insertion process.

FIG. 1 illustrates a schematic side view of one embodiment of a transcutaneous sensor device 100 configured to continuously measure analyte concentration (e.g., glucose concentration) in a host to provide a data stream representative of the host's analyte concentration, in accordance with the present embodiments. Sensors such as the one illustrated in FIG. 1 are sometimes referred to as "tack" sensors, due to their resemblance to a thumbtack.

In the particular embodiment illustrated in FIG. 1, the sensor device 100 comprises an in vivo portion 102 (also referred to as a sensor unit) configured for insertion under the host's skin 104, and an ex vivo portion 106 configured to remain above the host's skin surface after sensor insertion. The in vivo portion 102 comprises a tissue-piercing element 108 configured for piercing the host's skin 104, and a sensor body 110. The sensor body 110 comprises a support member 112 including one or more electrodes, and a membrane 114 disposed over at least a portion of the support member 112. The support member 112 may also be referred to as a sensor body 112, and the two terms are used interchangeably herein.

The ex vivo portion 106 comprises a mounting unit 116 that may include a sensor electronics unit (not shown) embedded or detachably secured therein, or alternatively may be configured to operably connect to a separate sensor electronics unit. Further details regarding the sensor device 100 and its components may be found in U.S. Patent Application Publication No. 2011/0077490, the disclosure of which is incorporated herein in its entirety.

Tissue-Piercing Element

The tissue-piercing element 108 of the sensor device 100 is configured to pierce the host's skin 104, and to open and define a passage for insertion of the sensor body 110 into a tissue of the host. In some embodiments, the tissue-piercing element 108 may be integral with the support member 112. In other embodiments, the tissue-piercing element 108 may be a discrete component. In such embodiments, the tissue-piercing element 108 may be secured to the support member 112, such as with an adhesive. Alternatively, the tissue-piercing element 108 may merely abut a blunt distal face of the support member 112 and/or the membrane 114. In such embodiments, an outer sleeve or band (not shown) may encircle a junction of the tissue-piercing element 108 and the support member 112/membrane 114.

The skin generally comprises multiple layers, including the epidermis, dermis, and subcutaneous layers. The epidermis comprises a number of layers within its structure including the stratum corneum, which is the outermost layer and is generally from about 10 to 20 microns thick, and the stratum germinativum, which is the deepest layer of the epidermis. While the epidermis generally does not contain blood vessels, it exchanges metabolites by diffusion to and from the dermis. While not wishing to be bound by theory, it is believed that because the stratum germinativum is supported by vascularization for survival, the interstitial fluid at the stratum germinativum sufficiently represents a host's analyte (e.g., glucose) levels. Beneath the epidermis is the dermis, which is from about 1 mm to about 3 mm thick and contains blood vessels, lymphatics, and nerves. The subcutaneous layer lies underneath the dermis and is mostly comprised of fat. The subcutaneous layer serves to insulate the body from temperature extremes. It also contains connective tissue and a small amount of blood vessels.

In some embodiments, the in vivo portion 102 of the sensor device 100 may have a length long enough to allow for at least a portion of the sensor body 110 to reside within the stratum germinativum. This may be desirable in some instances because the epidermis does not contain a substantial number of blood vessels or nerve endings. Thus, sensor insertion may be relatively painless, and the host may not experience much bleeding or discomfort from the insertion. In some of these embodiments, the in vivo portion 102 of the sensor device 100 may have a length of from about 0.1 mm to about 1.5 mm, or from about 0.2 mm to about 0.5 mm. In other embodiments, the in vivo portion 102 of the sensor device 100 may have a length that allows for at least a portion of the sensor body 110 to reside in the dermis layer. This may be desirable in some instances because the dermis is well vascularized, as compared to the subcutaneous layer, and thus may provide sufficient analytes (e.g., glucose) for measurement and reduce measurement lags associated with changes of analyte concentrations of a host, such as those that occur after meals. The metabolically active tissue near the outer dermis (and also the stratum germinativum) provides rapid equilibrium of the interstitial fluid with blood. In some of these embodiments, the in vivo portion 102 of the sensor device may have a length of from about 1 mm to about 7 mm, or from about 2 mm to about 6 mm. In still other embodiments, the in vivo portion 102 of the sensor device 100 may have a length that allows for at least a portion of the sensor body 110 to reside in the subcutaneous layer. While not wishing to be bound by theory, it is believed that because the subcutaneous layer serves to insulate the body from temperature extremes, the subcutaneous layer may reduce variations of analyte concentration readings associated with temperature fluctuations. In some of these embodiments, the in vivo portion 102 of the sensor device may have a length of from about 3 mm to about 10 mm, or from about 5 mm to about 7 mm.

Figure 2A:
FIGS. 2A-2H are schematic side views of example shapes of tissue-piercing tips for a continuous analyte sensor according to the present embodiments.
Figure 2B:
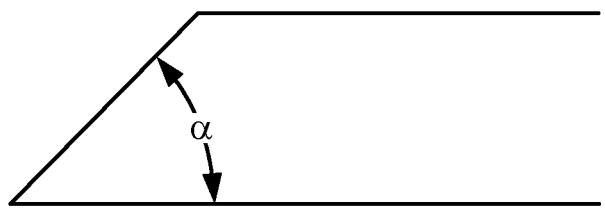
Figure 2C:
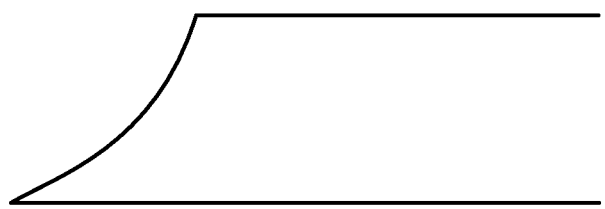
Figure 2D:
Figure 2E:
Figure 2F:
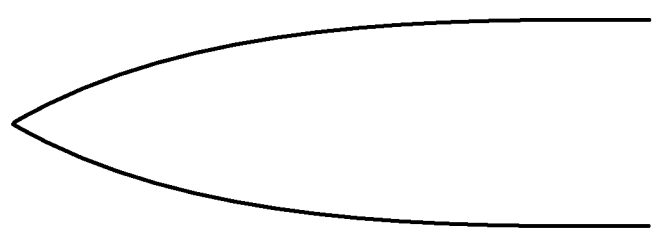
Figure 2G:
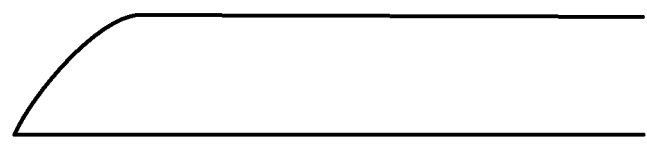
Figure 2H:

The tissue-piercing element may have any of a variety of geometric shapes and dimensions, including ones that minimize tissue trauma and reduce the force required for skin penetration. For example, in some embodiments, the tissue-piercing element may comprise a substantially conically-shaped distal tip, as illustrated in FIG. 1, such that the cross-sectional dimensions (e.g., diameter) of the tissue-piercing element tapers to a point 118 at the distal end of the tip, thereby providing a sharpened leading edge configured to facilitate skin penetration. As illustrated in FIG. 2B, in other embodiments, the distal tip of the tissue-piercing element may be beveled with a bevel angle $\alpha$, such as, for example, an angle of from about 5° to about 66°, or from about 10° to about 55°, or from about 40° to about 50°. In further embodiments, one or more surfaces of the tip may be curved, such as illustrated in FIGS. 2C-2H and 3D, so as to facilitate skin penetration when the sensor device is pushed downwards. In some embodiments, a curved surface may be advantageous because it provides the tissue-piercing element with a greater cutting surface area than a straight surface, and thus provides a smoother and more controlled insertion of the sensor unit through the skin. Also, a tissue-piercing element with a curved surface may cause less trauma to the pierced tissue than one with a straight surface.

The tissue-piercing element of the sensor device is designed to have appropriate flexibility and hardness and sufficient column strength to allow it to remain intact and to prevent it from substantial buckling during insertion of the in vivo portion of the sensor device through the skin of the host. Any of a variety of biocompatible materials having these characteristics may be used to form the tissue-piercing element, including, but not limited to, metals, ceramics, semiconductors, organics, polymers, composites, and combinations or mixtures thereof. Metals that may be used include stainless steel (e.g., 18-8 surgical steel), nitinol, gold, silver, nickel, titanium, tantalum, palladium, gold, and combinations or alloys thereof, for example. Polymers that may be used include polycarbonate, polymethacrylic acid, ethylenevinyl acetate, polytetrafluorethylene (TEFLON®), and polyesters, for example. In some embodiments, the tissue-piercing element may serve as a reference electrode and comprise a conductive material, such as a silver-containing material, for example. In certain embodiments, the tissue-piercing element has sufficient column strength to allow the user to press the sensor unit through the skin using the force from a thumb or finger, without substantial buckling of the tissue-piercing element. Accordingly, the structure of the tissue-piercing unit does not fail when it is subjected to resistance (e.g., axial force) associated with the penetration of tissue and skin. In some embodiments, the tissue-piercing element may have a column strength capable of withstanding an axial load greater than about 0.5 Newtons, or greater than about 1 Newton, or greater than about 2 Newtons, or greater than about 5 Newtons, or greater than about 10 Newtons, without substantial buckling. Often, an increase in the column thickness of an object will also increase its column strength. In some embodiments, the base 120 of the distal tip may have an outside diameter of from about 0.05 mm to about 1 mm, or from about 0.1 mm to about 0.5 mm, or from about 0.15 mm to about 0.3 mm, to provide the desired column strength for the tissue-piercing element.

Some of the tissue-piercing elements described herein are configured to protect the membrane of the sensor body. As described elsewhere herein, the membrane may be relatively delicate, and thus may be damaged during insertion of the sensor unit into the host. Consequently, any damage sustained by the membrane may affect the sensor device's performance and its ability to function properly. For example, in some embodiments one or more portions of the tissue-piercing element 108 may be formed with a cross-sectional area (along a plane transverse to the longitudinal axis of the tissue-piercing element 108) larger than that of the sensor body 110. By having a cross-sectional area larger than that of the sensor body 110, the tissue-piercing element 108 of the sensor device 100 is configured to pierce the host's skin 104 and to open and define a passage for insertion of the sensor body 110 into the tissue. Thus, the risk of a penetration-resistance force damaging and/or stripping the membrane 140 off from the rest of the sensor body 110 during the insertion process is reduced. In some embodiments, the largest dimension of the cross section transverse to a longitudinal axis of the tissue-piercing element 108 is less than about 0.1 mm, or less than about 0.05 mm, or less than about 0.03 mm.

In some embodiments, one or more layers of one or more polymers and/or bioactive agents may be coated onto the tissue-piercing element. The use of bioactive agents to coat the surface of the tissue-piercing element may provide a release of bioactive agents in the subcutaneous tissue during and/or after insertion of the in vivo portion of the sensor device. In further embodiments, one or more polymer layers may be used to control the release rate of the one or more bioactive agents. Such polymers may include, but are not limited to, parylene, parylene C, parylene N, parylene F, poly(hydroxymethyl-p-xylylene-co-p-xylylene) (PHPX), poly(lactic-co-glycolic acid) (PLGA), polyethylene-co-vinyl acetate (PEVA), Poly-L-lactic acid (PLA), poly N-butyl methacrylate (PBMA), phosphorylcholine, poly(isobutylene-co-styrene), polyoxyethylene (POE), polyglycolide (PGA), (poly(L-lactic acid), poly(amic acid) (PAA, polyethylene glycol (PEG), derivatives of one or more of these polymers, and combinations or mixtures thereof.

In some embodiments, one or more regions of the surface of the tissue-piercing element may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and dimensions, in accordance with the intended application. Use of reservoirs or depots may increase the amount of bioactive agents the tissue-piercing element is capable of carrying and delivering. In further embodiments, the tissue-piercing element may be hollow with a cavity and connected via various passages with one or more openings on its surface, so that bioactive agents may be released from the cavity via the openings. In some embodiments, for example as shown FIGS. 3A and 3B, the tissue-piercing element 310 comprises a pocket 312 shaped and dimensioned to support a sensor 314 with a membrane disposed thereon.

In certain embodiments, the in vivo portion of the sensor device is configured to remain substantially stationary within the tissue of the host, so that migration or motion of the sensor body with respect to the surrounding tissue is inhibited. Migration or motion may cause inflammation at the sensor implant site due to irritation, and may also cause noise on the sensor signal due to motion-related artifacts. Therefore, it may be advantageous to provide an anchoring mechanism that provides support for the in vivo portion of the sensor device to avoid the aforementioned problems. In some embodiments, the tissue-piercing element may comprise a surface with one or more regions that are textured. Texturing may roughen the surface of the tissue-piercing element and thereby provide a surface contour with a greater surface area than that of a non-textured (e.g., smooth) surface. Accordingly, the amount of bioactive agents, polymers, and/or coatings that the tissue-piercing element may carry and be released in situ is increased, as compared to that with a non-textured surface. Furthermore, it is believed that a textured surface may also be advantageous in some instances, because the increased surface area may enhance immobilization of the in vivo portion of the sensor device within the tissue of the host. In certain embodiments, the tissue-piercing element may comprise a surface topography with a porous surface (e.g. porous parylene), ridged surface, etc. In certain embodiments, the anchoring may be provided by prongs, spines, barbs, wings, hooks, a bulbous portion (for example, at the distal end), an S-bend along the tissue-piercing element, a gradually changing diameter, combinations thereof, etc., which may be used alone or in combination to stabilize the sensor within the subcutaneous tissue. For example, in certain embodiments, the tissue-piercing element may comprise one or more anchoring members configured to splay outwardly (e.g., in a direction toward a plane perpendicular to the longitudinal axis of the sensor unit) during or after insertion of the sensor unit. Outward deployment of the anchoring member facilitates anchoring of the sensor unit, as it results in the tissue-piercing element pressing against the surrounding tissue, and thus reduces (or prevents) movement and/or rotation of the sensor unit. In some embodiments, the anchoring members are formed of a shape memory material, such as nitinol, which may be configured to transform from a martensitic state to an austenitic state at a specific temperature (e.g., room temperature or body temperature). In the martensitic state, the anchoring members are ductile and in a contracted configuration. In the austenitic state, the anchoring members deploy to form a larger predetermined shape while becoming more rigid. While nitinol is described herein as an example of a shape memory material that may be chosen to form the anchoring member, it should be understood that other similar materials (e.g., shape memory material) may also be used.

The tissue-piercing element of the sensor device may be introduced subcutaneously at any of a variety of angles with respect to the mounting surface (the bottom surface of the mounting unit), and thus the skin surface. For example, in some embodiments the distal tip of the tissue-piercing element may extend substantially perpendicular to the mounting surface, but in other embodiments, the distal tip may extend at an angle with respect to the mounting surface of about 15°, 20°, 30°, 40°, 45°, 60°, 75°, 80°, 90°, 105°, 100°, 120°, 135°, 140°, 150°, 160°, or 165°, for example.

In alternative embodiments, to provide protection of the membrane during insertion of the sensor device, the sensor body may be embedded or encapsulated in a needle formed of a biodegradable material. Following insertion, the needle gradually biodegrades, leaving behind the sensor body which may then be activated. Any of a variety of biodegradable materials (e.g., a non-interfering carbohydrate) may be used. In some embodiments, the biodegradable material may include a certain concentration of an analyte to be measured, so that an initial calibration point of the sensor device may be provided.

As illustrated in FIG. 1, the sensor device 100 may include a skin-contacting mounting unit 116 configured to be secured to a host. In some embodiments, the mounting unit 116 comprises a base 122 adapted for fastening to a host's skin. The base 122 may be formed from a variety of hard or soft materials and may comprise a low profile for reducing protrusion of the sensor device from the host during use. In some embodiments, the base 122 is formed at least partially from a flexible material configured to conform to skin contour, so as to reduce or eliminate motion-related artifacts associated with movement by the host. In certain embodiments, the base 122 of the mounting unit 116 includes an adhesive material or adhesive layer 124, also referred to as an adhesive pad, preferably disposed on the mounting unit's bottom surface, and may include a releasable backing layer (not shown). Thus, removing the backing layer and pressing the base 122 of the mounting unit 116 onto the host's skin 104 adheres the mounting unit 116 to the host's skin 104. Appropriate adhesive layers may be chosen and designed to stretch, elongate, conform to, and/or aerate the region (e.g. host's skin). In some embodiments, the mounting unit comprises a guiding portion (not shown) configured to guide insertion of the sensor device 100 through the host's skin 104 and to support a column strength of the support member 112 such that the sensor device 100 is capable of being inserted through the host's skin 104 without substantial buckling.

Figure 3A:
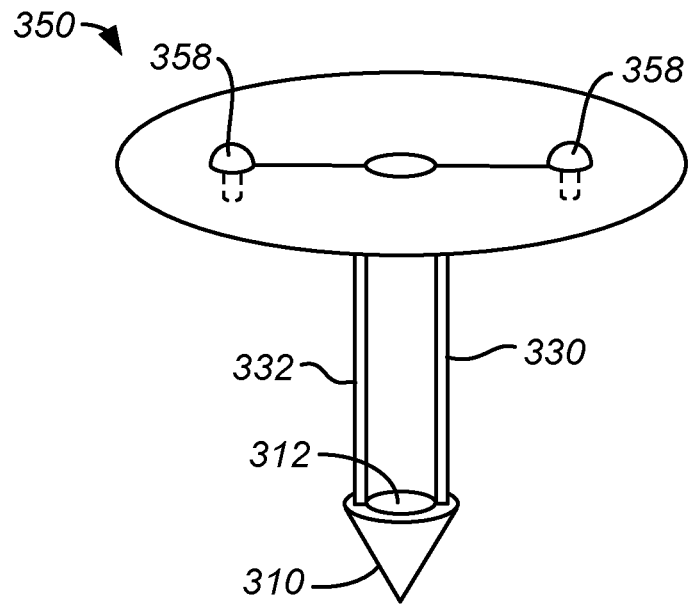
FIGS. 3A-3D are top perspective views of additional continuous analyte sensors according to the present embodiments.
Figure 3B:
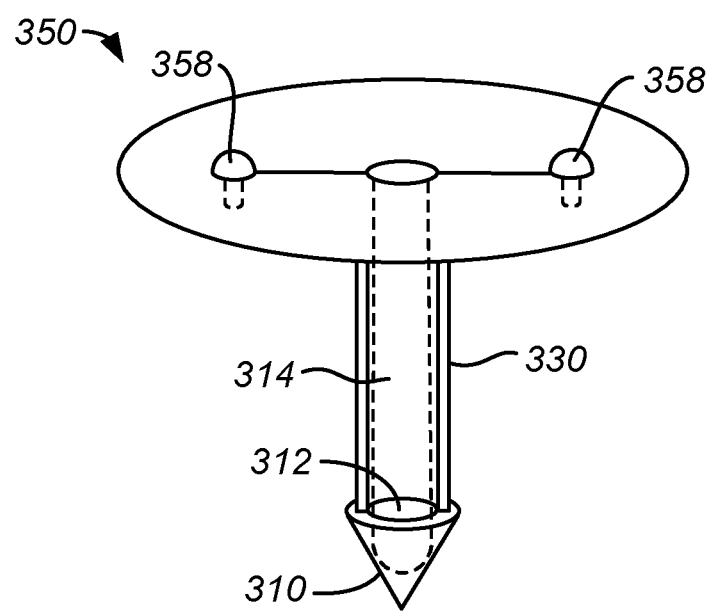
Figure 3C:
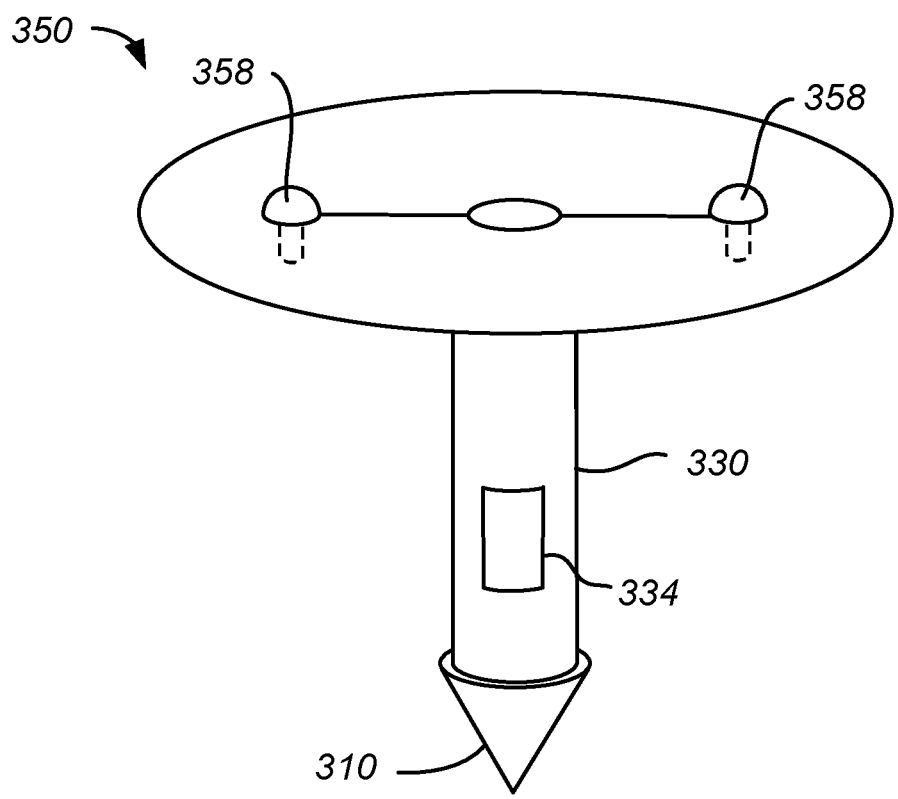
Figure 3D:
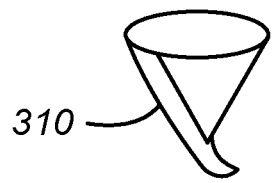

While FIG. 1 illustrates one configuration for providing membrane protection, other sensor body configurations may also be used. For example, some of the sensor bodies described herein may include a support member 330 configured to partially surround a sensor, as illustrated in FIGS. 3A and 3B, or configured to substantially surround a sensor, as illustrated in FIG. 3C. Unlike other embodiments described elsewhere herein, in the embodiments illustrated in FIGS. 3A-3C, the support member 330 does not comprise a working electrode. Rather, one or more working electrodes are arranged as components distinct from the support member 330. In some embodiments, the support member 330 may also serve as a reference electrode.

In the embodiment illustrated in FIG. 3A, the support member 330 comprises a longitudinal recess 332 configured to at least partially accommodate a sensor (e.g., a working electrode with a membrane disposed thereon). In some embodiments, the longitudinal recess may have a length corresponding to less than about 90% of the length of the support member 330, or less than about 75%, or less than about 50%, or less than about 33%, or less than about 25%. In other embodiments, the longitudinal recess may extend substantially across the entire length of the support member 330, as illustrated in FIG. 3B. In certain embodiments, the support member 330 may surround more than about 10% of the outer perimeter (e.g., circumference) of the sensor, or more than about 25%, or more than about 33%, or more than about 50%, or more than about 75%.

As illustrated in FIG. 3C, in some embodiments wherein the sensor (e.g., the working electrode) is substantially surrounded by the support member 330. The support member 330 may be provided with one or more window portions 334 (openings or slots extending through the wall thickness of the support member 330) that expose certain portions of the electrode to biological fluid (e.g., interstitial fluid), and thus allow biological fluid to diffuse toward and contact the working electrode's electroactive surface and the membrane disposed thereon. In this embodiment, the working electrode and the membrane disposed thereon are essentially housed within the support member 330, and are thus protected during packing, handling, and/or insertion of the device. The window portions 334 may have any of a variety of shapes and dimensions. For example, in some embodiments, the window portions may be formed to have a circular or substantially circular shape, but in other embodiments, the electrode may be formed with a shape resembling an ellipse, a polygon (e.g., triangle, square, rectangle, parallelogram, trapezoid, pentagon, hexagon, octagon), or the like. In certain embodiments, the window portions may comprise sections that extend around the perimeter of the longitudinal cross section of the support member. For example, the support member may be made by using a hypo-tube with window portions cut out in a spiral configuration, by ablation, etching, or other techniques.

Permeability

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. In some embodiments, from about 1, 2, 3, 4, or 5 picoAmps to about 25, 50, 100, 250, or 500 picoAmps of current is measured for every unit (mg/dl) of glucose measured.

Bioactive Agents

A variety of bioactive agents are known to promote fluid influx or efflux. Accordingly, incorporation of bioactive agents into the membrane may increase fluid bulk, bulk fluid flow, and/or diffusion rates (and promoting glucose and oxygen influx), thereby decrease non-constant noise. In some embodiments, fluid bulk and/or bulk fluid flow are increased at (e.g., adjacent to the sensor exterior surface) the sensor by incorporation of one or more bioactive agents. In some embodiments, the sensor is configured to include a bioactive agent that irritates the wound and stimulates the release of soluble mediators that are known to cause a local fluid influx at the wound site. In some embodiments, the sensor is configured to include a vasodilating bioactive agent, which may cause a local influx of fluid from the vasculature.

A variety of bioactive agents may be found useful in preferred embodiments. Example bioactive agents include but are not limited to blood-brain barrier disruptive agents and vasodilating agents, vasodilating agents, angiogenic factors, and the like. Useful bioactive agents include but are not limited to mannitol, sodium thiosulfate, VEGF/VPF, NO, NO-donors, leptin, bradykinin, histamines, blood components, platelet rich plasma (PRP), matrix metalloproteinases (MMP), Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Leptin, Copper Sulphate, Estradiol, prostaglandins, cox inhibitors, endothelial cell binding agents (for example, decorin or vimentin), glenipin, hydrogen peroxide, nicotine, and Growth Hormone. Still other useful bioactive agents include enzymes, cytotoxic or necrosing agents (e.g., pactataxyl, actinomycin, doxorubicin, daunorubicin, epirubicin, bleomycin, plicamycin, mitomycin), cyclophosphamide, chlorambucil, uramustine, melphalan, bryostatins, inflammatory bacterial cell wall components, histamines, proinflammatory factors and the like.

Bioactive agents may be added during manufacture of the sensor by incorporating the desired bioactive agent in the manufacturing material for one or more sensor layers or into an exterior biomaterial, such as a porous silicone membrane. For example, bioactive agents may be mixed with a solution during membrane formation, which is subsequently applied onto the sensor during manufacture. Alternatively, the completed sensor may be dipped into or sprayed with a solution of a bioactive agent, for example. The amount of bioactive agent may be controlled by varying its concentration, varying the indwell time during dipping, applying multiple layers until a desired thickness is reached, and the like, as disclosed elsewhere herein. In an alternative embodiment, the bioactive agent is microencapsulated before application to the sensor. For example, microencapsulated bioactive agent may be sprayed onto a completed sensor or incorporated into a structure, such as an outer mesh layer or a shedding layer. Microencapsulation may offer increased flexibility in controlling bioactive agent release rate, time of release occurrence and/or release duration.

Chemical systems/methods of irritation may be incorporated into an exterior sensor structure, such as the biointerface membrane (described elsewhere herein) or a shedding layer that releases the irritating agent into the local environment. For example, in some embodiments, a "shedding layer" releases (e.g., sheds or leaches) molecules into the local vicinity of the sensor and may speed up osmotic fluid shifts. In some embodiments, a shedding layer may provide a mild irritation and encourage a mild inflammatory/foreign body response, thereby preventing cells from stabilizing and building up an ordered, fibrous capsule and promoting fluid pocket formation.

A shedding layer may be constructed of any convenient, biocompatible material, include but not limited to hydrophilic, degradable materials such as polyvinylalcohol (PVA), PGC, Polyethylene oxide (PEO), polyethylene glycol-polyvinylpyrrolidone (PEG-PVP) blends, PEG-sucrose blends, hydrogels such as polyhydroxyethyl methacrylate (pHEMA), polymethyl methacrylate (PMMA) or other polymers with quickly degrading ester linkages. In certain embodiment, absorbable suture materials, which degrade to compounds with acid residues, may be used. The acid residues are chemical irritants that stimulate inflammation and wound healing. In certain embodiments, these compounds include glycolic acid and lactic acid based polymers, polyglactin, polydioxone, polydyconate, poly(dioxanone), poly(trimethylene carbonate) copolymers, and poly (caprolactone) homopolymers and copolymers, and the like.

In other example embodiments, the shedding layer may be a layer of materials listed elsewhere herein for the first domain, including copolymers or blends with hydrophilic polymers such as polyvinylpyrrolidone (PVP), polyhydroxyethyl methacrylate, polyvinylalcohol, polyacrylic acid, polyethers, such as polyethylene glycol, and block copolymers thereof including, for example, di-block, tri-block, alternating, random and graft copolymers (block copolymers are discussed in U.S. Pat. No. 4,803,243 and U.S. Patent). In one preferred embodiment, the shedding layer is comprised of polyurethane and a hydrophilic polymer. For example, the hydrophilic polymer may be polyvinylpyrrolidone. In one preferred embodiment, the shedding layer is polyurethane comprising not less than 5 weight percent polyvinylpyrrolidone and not more than 45 weight percent polyvinylpyrrolidone. Preferably, the shedding layer comprises not less than 20 weight percent polyvinylpyrrolidone and not more than 35 weight percent polyvinylpyrrolidone and, most preferably, polyurethane comprising about 27 weight percent polyvinylpyrrolidone.

In other example embodiments, the shedding layer may include a silicone elastomer, such as a silicone elastomer and a poly(ethylene oxide) and poly(propylene oxide) co-polymer blend, as disclosed in copending U.S. patent application Ser. No. 11/404,417 filed Apr. 14, 2006. In one embodiment, the silicone elastomer is a dimethyl- and methylhydrogensiloxane copolymer. In one embodiment, the silicone elastomer comprises vinyl substituents. In one embodiment, the silicone elastomer is an elastomer produced by curing a MED-4840 mixture. In one embodiment, the copolymer comprises hydroxy substituents. In one embodiment, the co-polymer is a triblock poly(ethylene oxide)-poly(propylene oxide)-poly(ethylene oxide) polymer. In one embodiment, the co-polymer is a triblock poly(propylene oxide)-poly(ethylene oxide)-poly(propylene oxide) polymer. In one embodiment, the co-polymer is a PLURONIC® polymer. In one embodiment, the co-polymer is PLURONIC® F-127. In one embodiment, at least a portion of the co-polymer is cross-linked. In one embodiment, from about 5% w/w to about 30% w/w of the membrane is the co-polymer.

A shedding layer may take any shape or geometry, symmetrical or asymmetrical, to promote fluid influx in a desired location of the sensor, such as the sensor head or the electrochemically reactive surfaces, for example. Shedding layers may be located on one side of sensor or both sides. In another example, the shedding layer may be applied to only a small portion of the sensor or the entire sensor.

In one example embodiment, a shedding layer comprising polyethylene oxide (PEO) is applied to the exterior of the sensor, where the tissue surrounding the sensor may directly access the shedding layer. PEO leaches out of the shedding layer and is ingested by local cells that release pro-inflammatory factors. The pro-inflammatory factors diffuse through the surrounding tissue and stimulate an inflammation response that includes an influx of fluid. Accordingly, early noise may be reduced or eliminated and sensor function may be improved.

In another example embodiment, the shedding layer is applied to the sensor in combination with an outer porous layer, such as a mesh or a porous biointerface as disclosed elsewhere herein. In one embodiment, local cells access the shedding layer through the through pores of a porous silicone biointerface. In one example, the shedding layer material is applied to the sensor prior to application of the porous silicone. In another example, the shedding layer material may be absorbed into the lower portion of the porous silicone (e.g., the portion of the porous silicone that will be proximal to the sensor after the porous silicone has been applied to the sensor) prior to application of the porous silicone to the sensor.

Wound Suppression

Non-constant noise may be decreased by wound suppression (e.g., during sensor insertion), in some embodiments. Wound suppression includes any systems or methods by which an amount of wounding that occurs upon sensor insertion is reduced and/or eliminated. While not wishing to be bound by theory, it is believed that if wounding is suppressed or at least significantly reduced, the sensor will be surrounded by substantially normal tissue (e.g., tissue that is substantially similar to the tissue prior to sensor insertion). Substantially normal tissue is believed to have a lower metabolism than wounded tissue, producing fewer interferents and reducing early noise.

Wounds may be suppressed by adaptation of the sensor's architecture to one that either suppresses wounding or promotes rapid healing, such as an architecture that does not cause substantial wounding (e.g., an architecture configured to prevent wounding), an architecture that promotes wound healing, an anti-inflammatory architecture, etc. In one example embodiment, the sensor is configured to have a low profile, a zero-footprint or a smooth surface. For example, the sensor may be formed of substantially thin wires, such as wires from about 50 µm to about 116 µm in diameter, for example. Preferably, the sensor is small enough to fit within a very small gauge needle, such as a 30, 31, 32, 33, 34, or 35 gauge needle (or smaller) on the Stubs scale, for example. In general, a smaller needle, the more reduces the amount of wounding during insertion. For example, a very small needle may reduce the amount of tissue disruption and thereby reduce the subsequent wound healing response. In an alternative embodiment, the sensor's surface is smoothed with a lubricious coating, to reduce wounding upon sensor insertion.

Wounding may also be reduced by inclusion of wound-suppressive agents (bioactive agents) that either reduce the amount of initial wounding or suppress the wound healing process. While not wishing to be bound by theory, it is believed that application of a wound-suppressing agent, such as an anti-inflammatory, an immunosuppressive agent, an anti-infective agent, or a scavenging agent, to the sensor may create a locally quiescent environment and suppress wound healing. In a quiescent environment, bodily processes, such as the increased cellular metabolism associated with wound healing, may minimally affect the sensor. If the tissue surrounding the sensor is undisturbed, it may continue its normal metabolism and promote sensor function.

In some embodiment, useful compounds and/or factors for suppressing wounding include but are not limited to first-generation $H_1$-receptor antagonists: ethylenediamines (e.g., mepyramine (pyrilamine), antazoline), ethanolamines (e.g., diphenhydramine, carbinoxamine, doxylamine, clemastine, and dimenhydrinate), alkylamines (pheniramine, chlorphenamine (chlorpheniramine), dexchlorphenamine, brompheniramine, and triprolidine), piperazines (cyclizine, hydroxyzine, and meclizine), and tricyclics (promethazine, alimemazine (trimeprazine), cyproheptadine, and azatadine); second-generation $H_1$-receptor antagonists such as acrivastine, astemizole, cetirizine, loratadine, mizolastine, azelastine, levocabastine, and olopatadine; mast cell stabilizers such as cromoglicate (cromolyn) and nedocromil; anti-inflammatory agents, such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (e.g., L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; corticosteroids such as cortisone, hydrocortisone, methylprednisolone, prednisone, prednisolone, betamethasone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone; immunosuppressive and/or immunomodulatory agents such as anti-proliferative, cell-cycle inhibitors (e.g., paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivastatin), E. coli heat-labile enterotoxin, and advanced coatings; anti-infective agents, such as anthelmintics (mebendazole); antibiotics such as aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim; interferent scavengers, such as superoxide dismutase (SOD), thioredoxin, glutathione peroxidase and catalase, anti-oxidants, such as uric acid and vitamin C, iron compounds, Heme compounds, and some heavy metals; artificial protective coating components, such as albumin, fibrin, collagen, endothelial cells, wound closure chemicals, blood products, platelet-rich plasma, growth factors and the like.

While not wishing to be bound by theory, it is believed that, in addition to the analyte sensor configurations described elsewhere herein, application of a lubricious coating to the sensor may substantially reduce and/or suppress noise occurrence by substantially preventing injury to the host. Accordingly, in some embodiments, a lubricious coating may be applied to the in vivo portion of the sensor to reduce the foreign body response to the implanted sensor. The term "lubricous coating" as used herein is used in its ordinary sense, including without limitation, a surface treatment that provides a reduced surface friction. A variety of polymers are suitable for use as a lubricious sensor coating, such as but not limited to Teflon, polyethylene, polycarbonate, polyurethane, poly(ethylene oxide), poly(ethylene oxide)-poly(propylene oxide) copolymers, and the like. In one example embodiment, one or more layers of HydroMed™, a polyether-polyurethane manufactured by CardioTech International, Inc. (Wilmington, MA) is applied to the sensor (e.g., over the resistance domain).

Dissolvable Tip

Sensors such as those described above are sometimes referred to as "tack" sensors, due to their resemblance to a thumbtack. One aspect of the present embodiments includes the realization that tack sensors include a sharpened tip that remains implanted in the tissue throughout the usable life of the sensor. Leaving the sharpened tip in vivo for an extended period of time may cause trauma to surrounding tissue, leading to scarring and inhibition of wound healing. Some of the present embodiments provide solutions to this problem. In some embodiments, the tip is configured to dissolve during the implantable sensor session, for example, within about 3, 5, 7 or 10 days.

As described above, and with reference to FIG. 1, the tissue-piercing element 108 may be a discrete component, separate from, for example, the sensor body 112. In such embodiments, the sensor body 112 may include a blunt tip or distal face 126. The tissue-piercing element 108 similarly includes a blunt proximal face 128 that abuts the sensor body tip 126. As described above, the tissue-piercing element 108 may or may not be secured to the sensor body 112.

In some embodiments, the tissue-piercing element 108 may comprise a biodegradable material, or a material that rapidly dissolves upon insertion into the host. Upon implantation, degradation of the tissue-piercing element 108 may be spontaneous with acid residues. In such embodiments, any sensor membrane(s) is desirably pH insensitive. A rate of degradation of the tissue-piercing element 108 depends upon the amount of tip material present. For example, the material may biodegrade/dissolve within three days after insertion into the host, or within two days, or one day, or twelve hours, or six hours, or three hours, or two hours, or one hour. In certain embodiments, the material may dissolve within a timeframe before which the sensor begins operating. In such embodiments, the dissolved material of the tissue-piercing element 108 may not interfere with sensor calibration.

Example materials for the tissue-piercing element 108 include at least one of a salt, a metallic salt, a sugar, a synthetic polymer, a glue or adhesive (such as cyanoacrylate), polylactic acid (PLA), polyglycolic acid, poly(lactic-co-glycolic acid) (PLGA), a polyanhydride, a polyphosphazene, or any material with glass-like properties. In particular, PLA, PLGA, and polyanhydrides all have sufficient hardness for this type of application. For example, a hardness of the tissue-piercing element 108 may be in the range of 35 D to 55 D, such as for example 45 D.

In some embodiments, the material of the tissue-piercing element 108 may be tuned or modified to achieve desired properties, such as dissolution time, hardness, etc. For example, the tissue-piercing element 108 may be processed with annealing and hardening cycles, and/or cross-linking. Cross-linking may be, for example, light based, such as irradiation with UV light. In some embodiments, the tuning may comprise combining materials. For example, the hardness of the tissue-piercing element 108 may be improved by incorporating hydroxyapatite in a blend, similar to some bone implants. Such a blend dramatically increases hardness. Also, these inclusions tend to lead to faster dissolution times.

If a polymer material is selected for the tissue-piercing element 108, it may have a crystallinity, which can also be defined by a Rockwell Hardness. For example, the material may have a Rockwell Hardness of about 25 D-65 D, such as about 45 D. An adequate Rockwell Hardness enables the polymer to undergo various processing steps without tearing or damage to the polymer.

Figure 4:
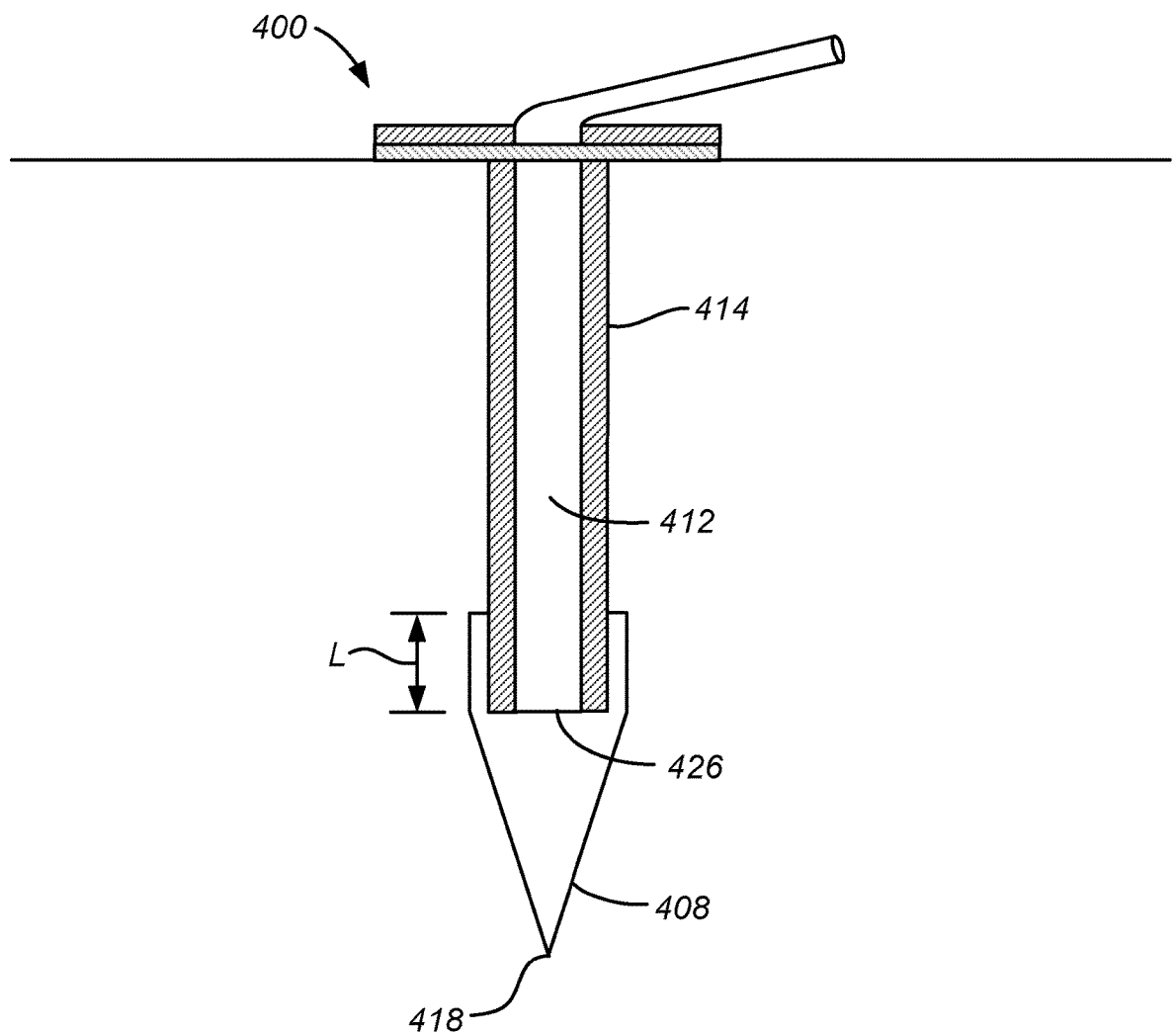
FIG. 4 is a continuous analyte sensor according to the present embodiments.

In some embodiments, the tissue-piercing element 108 may comprise a coating that covers at least a portion of the sensor body 112, including the sensor tip 126. For example, with reference to FIG. 4, a length L of the distal end of the sensor body 412 and membrane 414 may be dipped in a liquid bath (not shown). The length L may be chosen to coat enough of the sensor tip to achieve good adhesion without covering any electrodes on the sensor. For example, L may be in the range of 0.1-4 mm, such as 2-3 mm. As the sensor is withdrawn from the bath, the coating remains over the length L, and extends distally from the sensor body tip 426, forming a dissolvable tissue-piercing tip 408. After the coating cures, the portion extending from the sensor tip may be sharpened to produce a tissue-piercing coating tip 418.

In certain example embodiments, a viscosity of the liquid bath is below 100 cP, and the withdrawal rate is 20-30 in/sec, with an immediate exposure to UV (or heat) cross-linking to cure and build thickness. A tip mold or draw-through fixture that clamps and cures in one step in order to form a sharp cone shape is advantageous.

Another embodiment to create a sharp sensor tip with a polymer is to apply a voltage to the material while it is being cured. The voltage causes the polymer to modify its shape to a point. The sharp tip remains when the curing is completed and the voltage is removed. Curing could comprise irradiating, drying, heating, etc. Another embodiment comprises heating the material and drawing it out like glass.

As discussed above, the sensor 400 may include one or more aspects that either suppress wounding, or promote rapid healing, or both. In certain embodiments, these aspects may be present in the dissolvable tip 408. For example, one or more bioactive agents may be integrated into the dissolvable tip 408 by combining it with the material of the liquid bath during the dipping process. Alternatively, before or after curing, the dissolvable tip 408 may be dipped in a subsequent liquid bath that coats the dissolvable tip 408 with one or more bioactive agents. Example bioactive agents are discussed at length above and will not be repeated here. However, certain bioactive agents may, for example, induce osmotic pressure or oncotic pressure.

In certain embodiments, the material of the dissolvable tip 408 may have an effect on the sensor 400. For example, if the dissolvable tip 408 is a salt, it could set up an osmotic pressure gradient that may pull fluids to the tissue surrounding the sensor 400, causing it to startup faster or avoid early signal attenuation.

Dissolvable Needle

Some of the present embodiments relate to sensors that require a needle for insertion into the host. For example, with reference to FIG. 5, the sensor 500 may be contained within a lumen 504 of a needle 502. Another aspect of the present embodiments includes the realization that the need to remove the needle after sensor insertion adds complexity to the insertion process, including the need to electrically connect the sensor to sensor electronics after insertion. Some of the present embodiments provide solutions to this problem.

Figure 5:
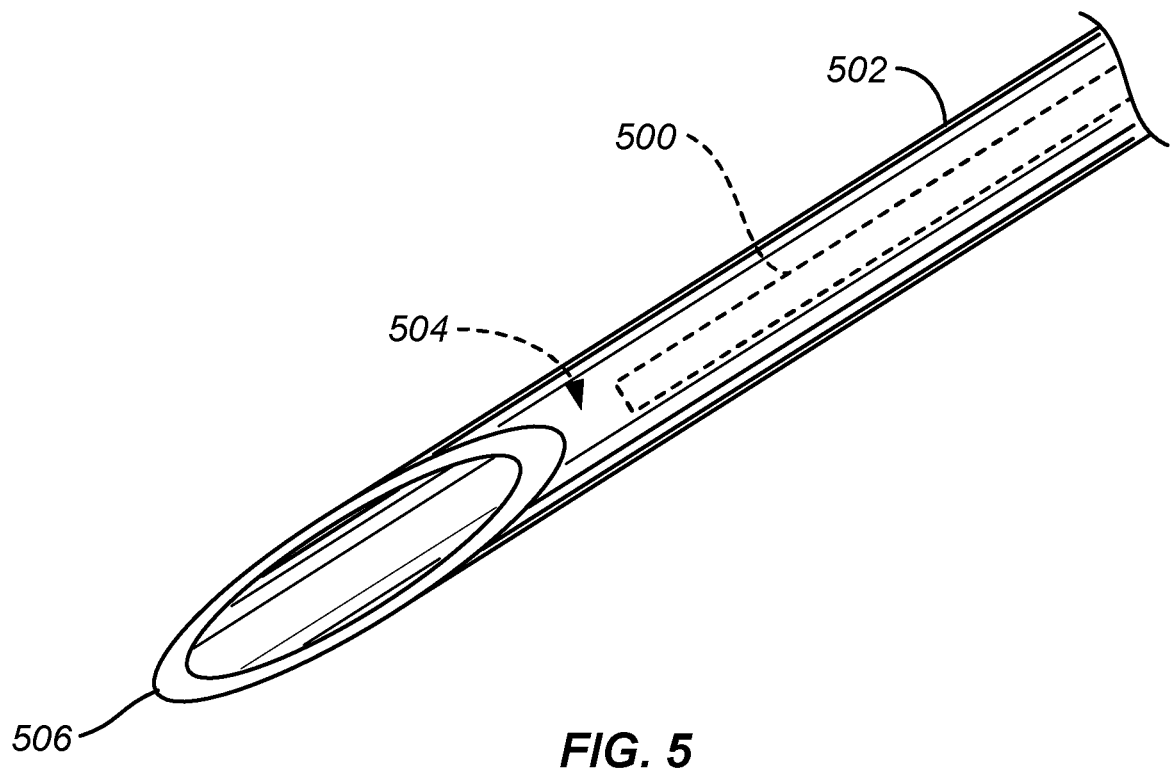
FIG. 5 is a front perspective view of a system for inserting a continuous analyte sensor into a host according to the present embodiments.

With reference to FIG. 5, the needle 502 may be similar to a standard hypodermic needle 502, including a lumen 504 and a sharp distal tip 506. However, the material of the needle 502 may be biodegradable, or capable of dissolving after insertion into a host. The material and material properties of the needle 502 may be similar to those discussed above with respect to the dissolvable tissue-piercing tip 506. These materials and material properties are discussed at length above, and will not be repeated here. However, polyanhydrides are one particularly advantageous material for the needle 502, as they may form tubes readily and those in turn may be sharpened by cutting.

Figure 6:
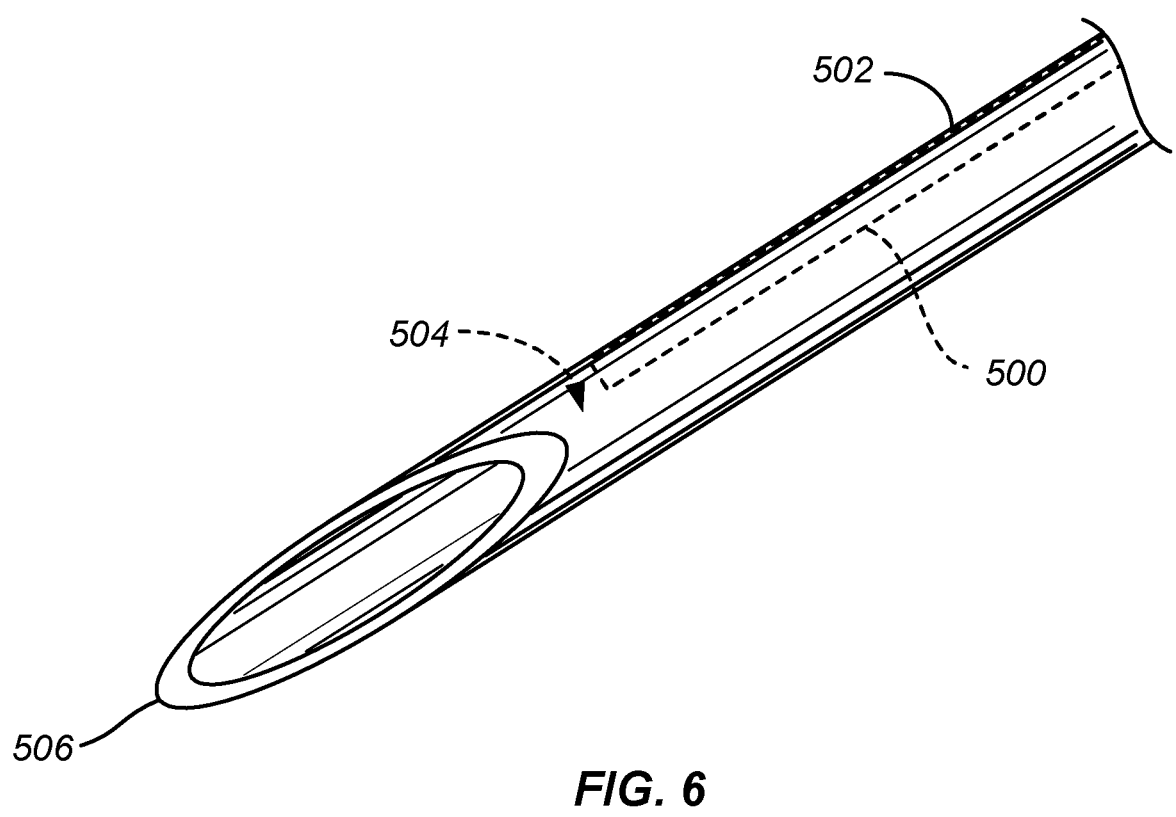
FIG. 6 is a front perspective view of another system for inserting a continuous analyte sensor into a host according to the present embodiments.

In some embodiments, the sensor 500 may be received within the lumen 504 but not attached to the needle 502 (FIG. 5), for example may be held via friction force within the needle and/or couple to a base, such as base 122 as shown in FIG. 1. In other embodiments, the sensor 500 may be attached to the needle 502 (FIG. 6) using mechanical or chemical coupling methodologies, as may be appreciated by one skilled in the art.

In the present embodiments, since the needle 502 is biodegradable/dissolvable, it does not need to be removed from the host after the sensor 500 is inserted. Instead, the needle 502 harmlessly biodegrades, thereby eliminating the traumatic tip 506 and leaving behind the sensor 500. The dissolvable needle 502 thus simplifies the process of inserting the sensor 500 into the host. In addition, since the needle 502 does not need to be withdrawn, the sensor 500 may be electrically connected to sensor electronics (not shown) prior to insertion. This aspect advantageously eliminates the need to connect the sensor 500 to sensor electronics after insertion, which may be challenging.

As with the embodiments of the dissolvable tissue-piercing tip 506 discussed above, the present dissolvable needle 502 may include one or more bioactive agents to suppress wounding and/or promote rapid wound healing. These bioactive agents may be similar to those discussed above, and may be applied to/integrated into the needle 502 using the same techniques discussed above.

In certain embodiments, the needle 502 may be at least partially dissolvable. In such embodiments, the needle may have stronger and weaker (or more and less dissolvable) portions, such that in vivo the weaker portions dissolve more quickly and the stronger portions then break away from one another. The stronger portions may ultimately dissolve, albeit more slowly than the weaker portions. Such embodiments may be described as "fractionate," referring to how the weaker portions dissolve quickly allowing the hard segments, such as PLA or PGA, that provide sufficient strength during insertion, to fragment away, while not harming the body during or after sensor insertion.

Membrane Hardening Agent

One aspect of the present embodiments includes the realization that the material of analyte sensor membranes is soft, and tends to peel back as the sensor advances into tissue. This problem is especially acute for sensors that are formed by a process in which they are first coated with a membrane and then sharpened at the tip. This process exposes the sensor body, and leaves a thin coating of the membrane surrounding the sides of the sensor body at the tip. Some of the present embodiments provide solutions to this problem.

Figure 7:
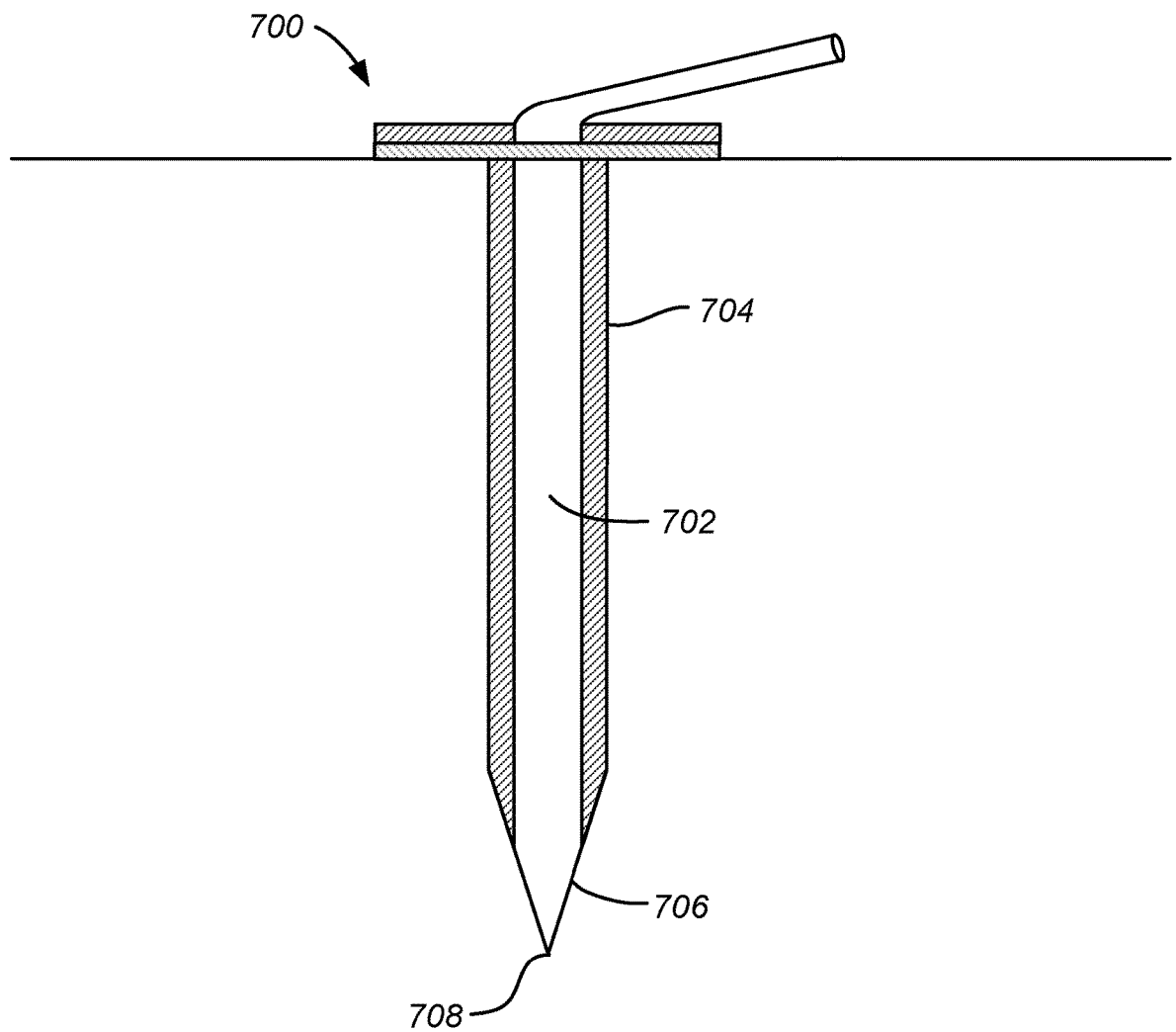
FIG. 7 is a continuous analyte sensor according to the present embodiments.

FIG. 7 illustrates a sensor unit 700 similar to the sensor device 100 described above and shown in FIG. 1. The sensor unit 700 includes a sensor body 702 at least partially covered by a membrane 704. Rather than having a discrete tissue-piercing element, as in the previous embodiments, instead the distal end 706 of the sensor body 702 and membrane 704 are sharpened to form a tissue-piercing tip 708. Since the sensor is sharpened after being coated with the membrane 704, a portion of the sensor body 702 is exposed at the sharpened tip 708. In an alternative embodiment illustrated in FIG. 8, the sensor body 802 may be sharpened prior to being coated with the membrane 804, so that the sharpened tip 808 is covered with membrane 804.

Figure 8:
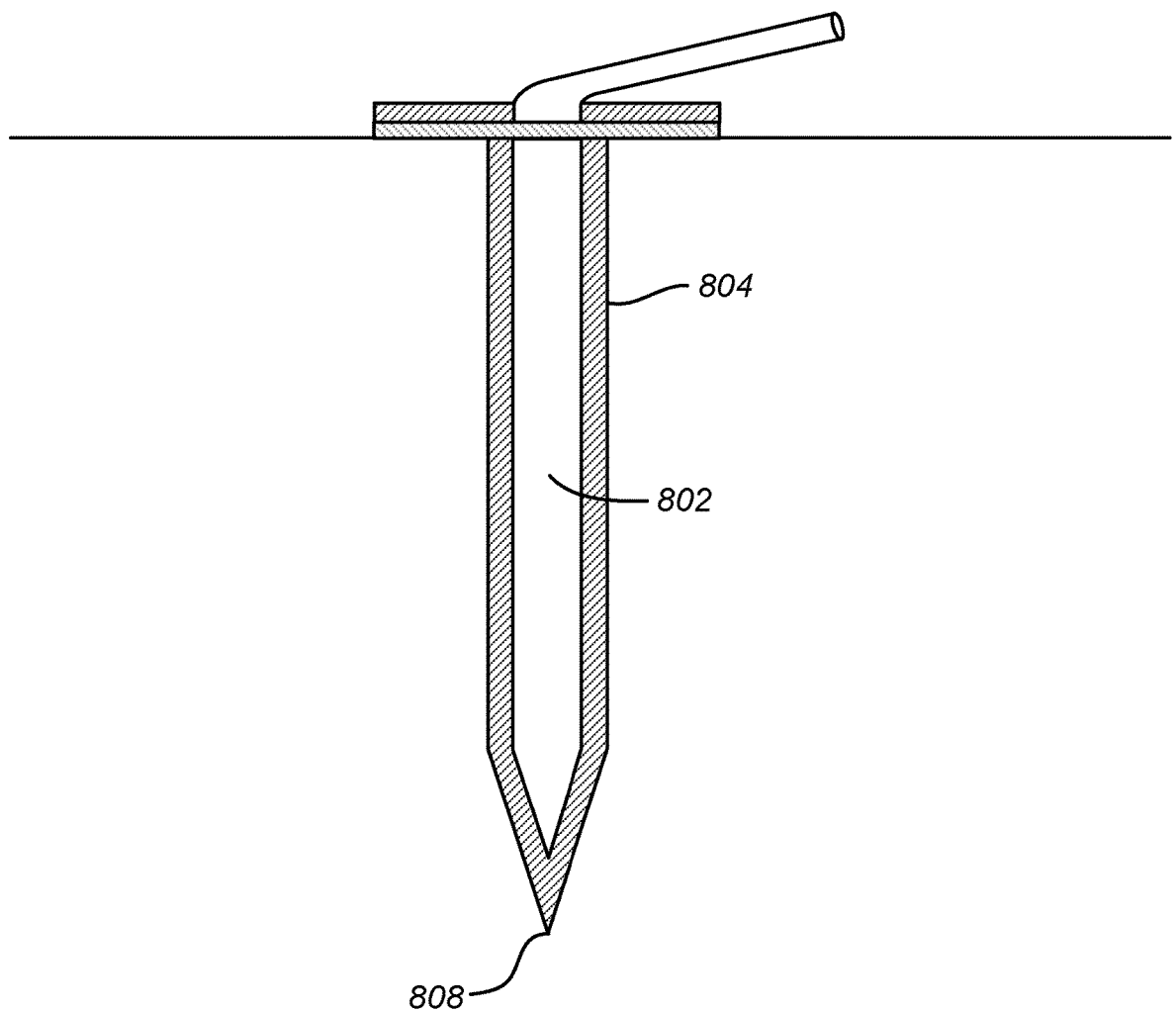
FIG. 8 is a continuous analyte sensor according to the present embodiments.

In both of the embodiments illustrated in FIGS. 7 and 8, the soft membrane 704, 804 is susceptible to peeling back as the sensor advances through tissue during the process of being inserted into the host. Also, due to its very small diameter, the sensor of FIGS. 7 and 8 may lack the column strength necessary to be inserted through the host's skin without substantial buckling. To solve these problems, certain of the present embodiments provide a hardening agent 900 that either covers the membrane 902 (FIG. 9) or is integrated into the membrane 902 (FIG. 10). The hardening agent 900 provides increased column strength to the sensor body 904 so that the sensor unit 906 is capable of being inserted through the host's skin 908 without substantial buckling. The hardening agent 900 may also increase adhesion of the membrane 902 to the sensor body 904 and/or stiffen the membrane 902 so that it is more resistant to peeling back as the sensor advances through tissue during the process of being inserted into the host. Preferably, however, the hardening agent 900 allows analyte permeability within the membrane 902 so that the ability of the sensor to function is not compromised.

Figure 9:
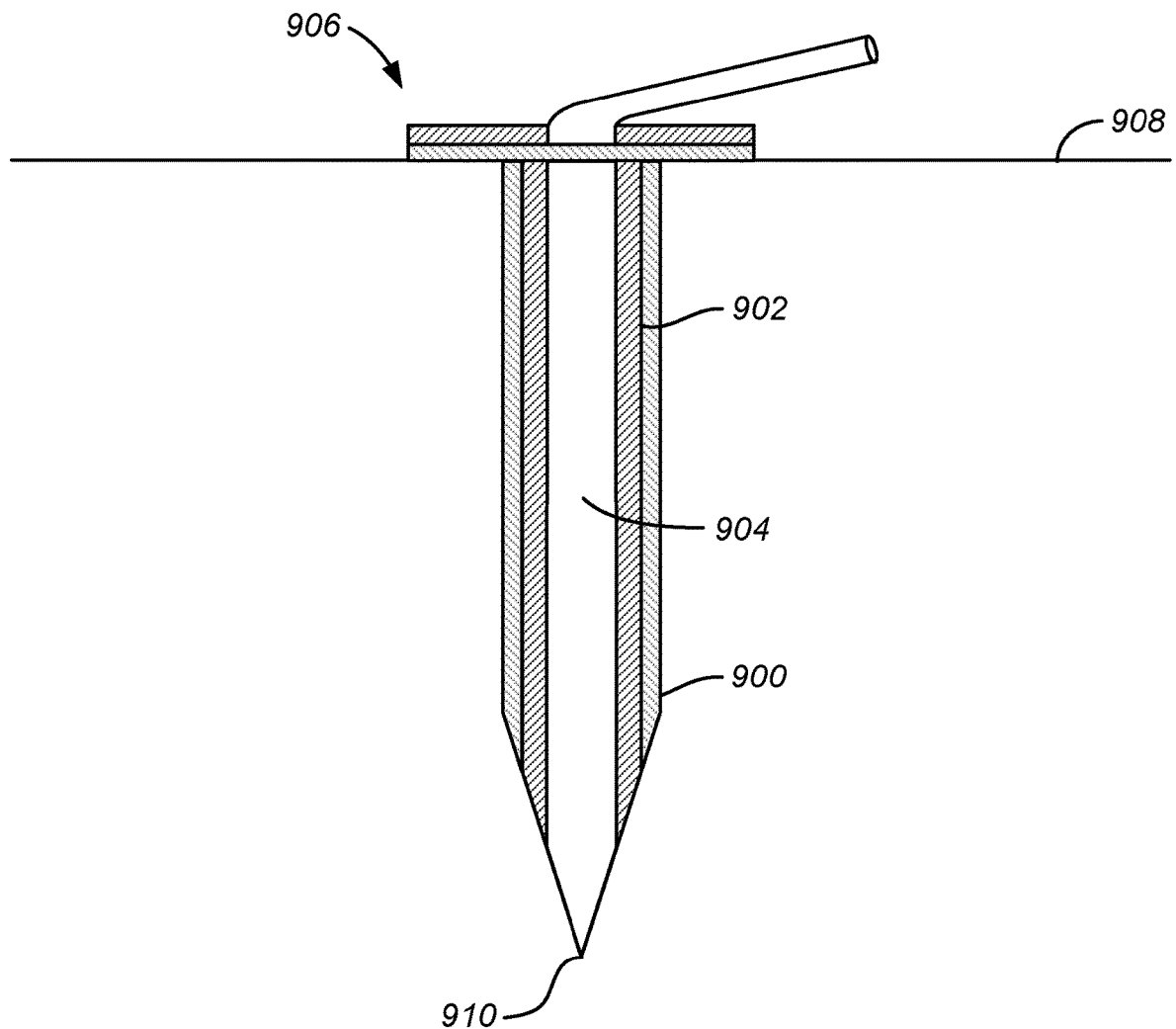
FIG. 9 is a continuous analyte sensor according to the present embodiments.
Figure 10:
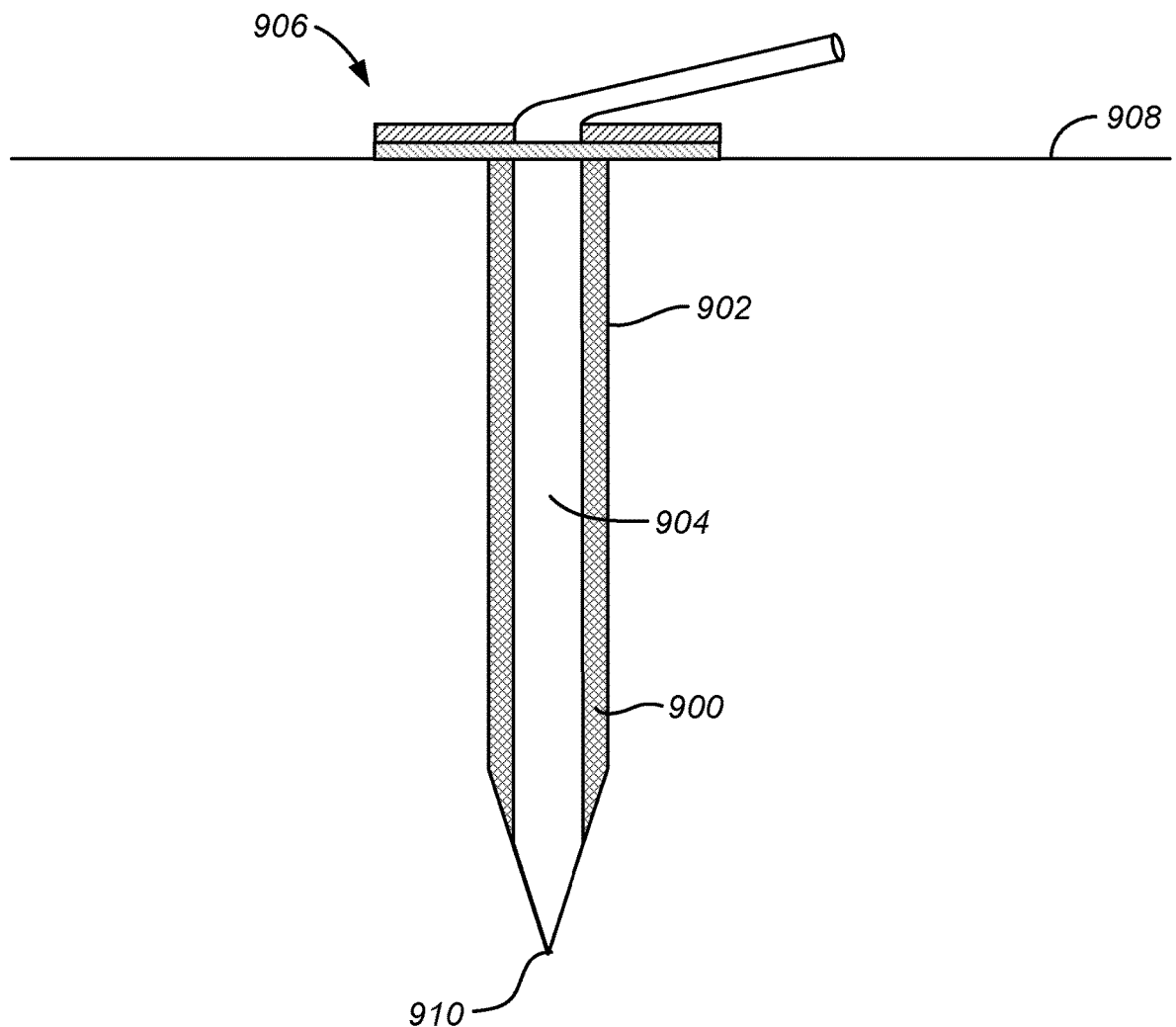
FIG. 10 is a continuous analyte sensor according to the present embodiments.

While FIGS. 9 and 10 illustrate embodiments in which a tip 910 of the sensor body 904 is exposed through the membrane 902/hardening agent 900, the present embodiments also contemplate that the tip 910 of the sensor body 904 could be covered by the membrane 902/hardening agent 900, similar to the embodiment of FIG. 8. Where the tip 910 of the sensor body 904 is exposed through the membrane 902/hardening agent 900, in certain embodiments the material of sensor body 904 is selected so that it does not react with a selected analyte and/or product of an analyte reaction. Such a reaction may create background current, which may adversely affect the performance of the sensor.

In one embodiment, the material of the sensor body 904 may be formed with a core that does not react with hydrogen peroxide. One such sensor body is platinum cladding on tantalum, where the tantalum core does not react with hydrogen peroxide or create additional background signal due to its electrochemical properties. The small amount of exposed platinum may not significantly contribute to the background signal.

In certain embodiments, the hardening agent 900 comprises cyanoacrylate. Cyanoacrylate is an advantageous material to use for this application, because it may permeate into the membrane, it cures quickly, it is very hard, and it may be machined after curing if needed. Cyanoacrylate may also deaden any enzyme that is on the tip, and coat any electrochemically active surfaces. Other example materials include epoxies and UV adhesives.

In one embodiment, a method of making a sensor device comprises coating a wire with a membrane. The coated wire is then cut to a desired length to form a sensor wire having a tip. Example methods for performing these steps are described in U.S. Patent Application Publication No. 2011/0027453, the entire contents of which are hereby incorporated by reference herein. The coated sensor wire is then exposed to a hardening agent such that the membrane absorbs the hardening agent. Then, if necessary, the hardening agent is cured.

Exposing the coated sensor wire to the hardening agent may comprise dipping at least the sensor tip in a liquid bath of the hardening agent. After the sensor wire is withdrawn from the liquid bath, the membrane is cured to harden the hardening agent. Thereafter, the sensor tip may be sharpened to form a sharp point capable of piercing tissue. In alternative embodiments, the sensor wire may be sharpened prior to applying the membrane to the sensor wire, or after applying the membrane to the sensor wire but prior to applying the hardening agent.

In embodiments in which the sensor tip is sharpened after the membrane and hardening agent are applied, a deadening agent may be applied to the sharpened sensor tip to deaden any active surfaces exposed during the sharpening step. For example, platinum (Pt) or enzyme layer may be considered "active surfaces." In some embodiments, the deadening agent may comprise cyanoacrylate or a silane. Silanes may be particularly advantageous, since they may be lubricious, which may help the sensor penetrate into skin.

In embodiments that include a deadening agent, the deadening agent may be applied using vapor deposition, such as chemical vapor deposition (CVD) or physical vapor deposition (PVD). For example, a two-step application process may be used comprising a masking agent and then a spray agent followed by a rinse cycle.

In another embodiment, a method of making a sensor device comprises coating a wire with a membrane. The coated wire is then cut to a desired length to form a sensor wire having a tip. The coated wire is then exposed to a hardening agent such that the hardening agent covers the membrane. Additional process steps may then proceed similar to those in the foregoing embodiment, such as curing, sharpening, etc.

In another embodiment, a method of making a sensor device comprises cutting a wire to a desired length to form a sensor wire having a tip. The sensor tip is then sharpened to form a sharp point capable of piercing tissue. The sensor wire is then coated, including the sharpened sensor tip, with a membrane. The coated sensor wire is then exposed to a hardening agent such that the membrane absorbs the hardening agent. Additional process steps may then proceed similar to those in the foregoing embodiment, such as curing, etc.

In another embodiment, a method of making a sensor device comprises cutting a wire to a desired length to form a sensor wire having a tip. The sensor tip is then sharpened to form a sharp point capable of piercing tissue. The sensor wire is then coated, including the sharpened sensor tip, with a membrane. By coating the membrane, the host's fluid is separated from the enzyme by the protective membrane system, avoiding leaching of the enzyme into the host and ensuring a controlled pathway of diffusion of the host's fluid through the membrane system, including the enzyme. The coated sensor wire is then exposed to a hardening agent such that the hardening agent covers the membrane. Additional process steps may then proceed similar to those in the foregoing embodiment, such as curing, etc.

In any of the foregoing embodiments, the wire may be a shape memory metal (or a more rigid metal like Ti). In such embodiments, the wire may be held in a first position, which may be curved or straight, and during the insertion process the wire returns to its memorized shape, which may be curved or straight. The return to the memorized shape may release stored spring energy in the wire, creating a whipping action that facilitates piercing the skin.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,077; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792, 562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,598; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0033132-A1; U.S. Patent Publication No. 2005-0051427-A1; U.S. Patent Publication No. 2005-0090607-A1; U.S. Patent Publication No. 2005-0176136-A1; U.S. Patent Publication No. 2005-0245799-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No. 2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No.

2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2005-0056552-A1; and U.S. Patent Publication No. 2005-0182451-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS"; U.S. application Ser. No. 12/828,967 filed on Jul. 1, 2010 and entitled "HOUSING FOR AN INTRAVASCULAR SENSOR"; U.S. application Ser. No. 13/461,625 filed on May 1, 2012 and entitled "DUAL ELECTRODE SYSTEM FOR A CONTINUOUS ANALYTE SENSOR"; U.S. application Ser. No. 13/594,602 filed on Aug. 24, 2012 and entitled "POLYMER MEMBRANES FOR CONTINUOUS ANALYTE SENSORS"; U.S. application Ser. No. 13/594,734 filed on Aug. 24, 2012 and entitled "POLYMER MEMBRANES FOR CONTINUOUS ANALYTE SENSORS"; U.S. application Ser. No. 13/607,162 filed on Sep. 7, 2012 and entitled "SYSTEM AND METHODS FOR PROCESSING ANALYTE SENSOR DATA FOR SENSOR CALIBRATION"; U.S. application Ser. No. 13/624,727 filed on Sep. 21, 2012 and entitled "SYSTEMS AND METHODS FOR PROCESSING AND TRANSMITTING SENSOR DATA"; U.S. application Ser. No. 13/624,808 filed on Sep. 21, 2012 and entitled "SYSTEMS AND METHODS FOR PROCESSING AND TRANSMITTING SENSOR DATA"; U.S. application Ser. No. 13/624,812 filed on Sep. 21, 2012 and entitled "SYSTEMS AND METHODS FOR PROCESSING AND TRANSMITTING SENSOR DATA"; U.S. application Ser. No. 13/732,848 filed on Jan. 2, 2013 and entitled "ANALYTE SENSORS HAVING A SIGNAL-TO-NOISE RATIO SUBSTANTIALLY UNAFFECTED BY NON-CONSTANT NOISE"; U.S. application Ser. No. 13/733,742 filed on Jan. 3, 2013 and entitled "END OF LIFE DETECTION FOR ANALYTE SENSORS"; U.S. application Ser. No. 13/733,810 filed on Jan. 3, 2013 and entitled "OUTLIER DETECTION FOR ANALYTE SENSORS"; U.S. application Ser. No. 13/742,178 filed on Jan. 15, 2013 and entitled "SYSTEMS AND METHODS FOR PROCESSING SENSOR DATA"; U.S. application Ser. No. 13/742,694 filed on Jan. 16, 2013 and entitled "SYSTEMS AND METHODS FOR PROVIDING SENSITIVE AND SPECIFIC ALARMS"; U.S. application Ser. No. 13/742,841 filed on Jan. 16, 2013 and entitled "SYSTEMS AND METHODS FOR DYNAMICALLY AND INTELLIGENTLY MONITORING A HOST'S GLYCEMIC CONDITION AFTER AN ALERT IS TRIGGERED"; and U.S. application Ser. No. 13/747,746 filed on Jan. 23, 2013 and entitled "DEVICES, SYSTEMS, AND METHODS TO COMPENSATE FOR EFFECTS OF TEMPERATURE ON IMPLANTABLE SENSORS".

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and 'one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of making a sensor device for measuring an analyte concentration in a host, the method comprising:
    coating a wire with a membrane;
    cutting the coated wire to a desired length to thereby form a sensor tip; and
    exposing the coated wire to a hardening agent such that the membrane absorbs the hardening agent, whereby the sensor device is formed, the sensor device being configured to be inserted into skin of the host and configured to measure the analyte concentration within the skin of the host.

2. The method of claim 1, wherein exposing the coated wire comprises dipping at least the sensor tip in the hardening agent.

3. The method of claim 1, further comprising curing the membrane to harden the hardening agent.

4. The method of claim 1, further comprising sharpening the sensor tip to form a sharp point capable of piercing tissue.

5. The method of claim 4, wherein the sensor tip comprises a material that does not react with hydrogen peroxide.

6. The method of claim 4, further comprising applying a deadening agent to the sharpened sensor tip to deaden any active surfaces exposed during the sharpening step.

7. The method of claim 6, wherein the deadening agent comprises cyanoacrylate or silane.

8. The method of claim 6, wherein the deadening agent is applied using vapor deposition.

9. The method of claim 4, further comprising sharpening the membrane at the sensor tip.

10. The method of claim 4, wherein the sharp point is exposed through the membrane.

11. The method of claim 1, wherein the hardening agent provides increased column strength to the coated wire such that the coated wire is capable of being inserted through the skin of the host without substantial buckling.

12. The method of claim 1, wherein the hardening agent increases adhesion of the membrane to the wire.

13. The method of claim 1, wherein the hardening agent allows analyte permeability within the membrane.

14. The method of claim 1, wherein the hardening agent promotes resistance to peeling of the membrane from the wire during insertion of the sensor device into the skin of the host.

15. The method of claim 1, wherein the hardening agent comprises cyanoacrylate.

16. The method of claim 1, wherein the hardening agent comprises an epoxy or an ultraviolet (UV) adhesive.

17. The method of claim 1, wherein the hardening agent is suspended in a matrix.

18. The method of claim 1, wherein the sensor device is configured to be inserted into the skin of the host with direct press insertion.

19. The method of claim 1, wherein the sensor device is configured to remain in vivo for measurement of the analyte concentration within the skin of the host and configured to be removed from the skin of the host.

20. The method of claim 1, further comprising coupling the wire to a mounting unit configured to remain ex vivo and adhere to a surface of the skin of the host when the sensor device is positioned within the skin of the host.

* * * * *